(12) United States Patent
Dasi et al.

(10) Patent No.: US 11,382,694 B2
(45) Date of Patent: Jul. 12, 2022

(54) SYSTEMS AND METHODS FOR PREDICTIVE HEART VALVE SIMULATION

(71) Applicant: Ohio State Innovation Foundation, Columbus, OH (US)

(72) Inventors: Lakshmi Dasi, Dublin, OH (US); Amirsepehr Azimian, Columbus, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 348 days.

(21) Appl. No.: 16/335,614

(22) PCT Filed: Oct. 4, 2017

(86) PCT No.: PCT/US2017/055046
§ 371 (c)(1),
(2) Date: Mar. 21, 2019

(87) PCT Pub. No.: WO2018/097902
PCT Pub. Date: May 31, 2018

(65) Prior Publication Data
US 2019/0298450 A1    Oct. 3, 2019

Related U.S. Application Data

(60) Provisional application No. 62/403,940, filed on Oct. 4, 2016.

(51) Int. Cl.
*A61B 34/10* (2016.01)
*G16H 50/50* (2018.01)
*A61B 5/00* (2006.01)
*A61B 5/026* (2006.01)
(Continued)

(52) U.S. Cl.
CPC .......... *A61B 34/10* (2016.02); *A61B 5/0044* (2013.01); *A61B 5/0263* (2013.01);
(Continued)

(58) Field of Classification Search
CPC ....... G06F 30/23; A61B 34/10; A61B 5/0044; A61B 5/0263; A61B 5/7275; A61B 6/03;
(Continued)

(56) References Cited

U.S. PATENT DOCUMENTS

| | | | |
|---|---|---|---|
| 2011/0153286 A1* | 6/2011 | Zaeuner | G06T 17/00 703/1 |
| 2015/0112659 A1* | 4/2015 | Mortier | A61B 34/10 703/11 |
| 2016/0191887 A1* | 6/2016 | Casas | G02B 27/0172 348/47 |

OTHER PUBLICATIONS

Wang et al. 2012 J. Biomechanics 45:1965-1971 (Year: 2012).*
(Continued)

*Primary Examiner* — Colin T. Sakamoto
*Assistant Examiner* — Patrick M Mehl
(74) *Attorney, Agent, or Firm* — Benesch, Friedlander, Coplan & Aronoff LLP

(57) ABSTRACT

Systems and methods are described herein for predictive heart valve simulation. The systems and methods described herein can include segmenting anatomical region of a heart of a patient from image data characterizing the heart of the patient. Anatomical model data that can include three-dimensional shapes of the anatomical regions of the heart can be generated based on the image data. The anatomical model data can be used to generate anatomical model data. The analytical model data can include a three-dimensional mesh of the anatomical regions of the heart. A deformed analytical model that can be indicative of a deformed position of the anatomical regions of the heart and a deformed position of the surgical object can be generated based on the analytical model data.

20 Claims, 33 Drawing Sheets

(51) Int. Cl.
| | |
|---|---|
| A61B 6/03 | (2006.01) |
| A61B 6/00 | (2006.01) |
| A61B 8/06 | (2006.01) |
| A61B 8/00 | (2006.01) |
| A61F 2/24 | (2006.01) |
| G06T 17/20 | (2006.01) |
| A61B 8/08 | (2006.01) |
| G16H 30/40 | (2018.01) |

(52) U.S. Cl.
 CPC .............. *A61B 5/7275* (2013.01); *A61B 6/03* (2013.01); *A61B 6/466* (2013.01); *A61B 6/503* (2013.01); *A61B 6/507* (2013.01); *A61B 6/5217* (2013.01); *A61B 8/065* (2013.01); *A61B 8/466* (2013.01); *A61B 8/483* (2013.01); *A61B 8/5223* (2013.01); *A61F 2/2427* (2013.01); *G06T 17/20* (2013.01); *G16H 30/40* (2018.01); *G16H 50/50* (2018.01); *A61B 6/504* (2013.01); *A61B 8/0883* (2013.01); *A61B 2034/104* (2016.02); *A61B 2034/105* (2016.02); *A61B 2034/108* (2016.02); *G06T 2210/41* (2013.01)

(58) Field of Classification Search
 CPC ......... A61B 6/466; A61B 6/503; A61B 6/507; A61B 6/5217; A61B 8/065; A61B 8/466; A61B 8/483; A61B 8/5223; A61B 6/504; A61B 8/0883; A61B 2034/104; A61B 2034/105; A61B 2034/108; G16H 30/40; G16H 50/50; A61F 2/2427; G06T 17/20; G06T 2210/41
 See application file for complete search history.

(56) References Cited

OTHER PUBLICATIONS

Tribouilloy et al. 2000 Circulation 102:558-564 (Year: 2000).*
Zheng et al. 2012 IEEE Transactions on Medical Imaging 31:2307-2321 (Year: 2012).*
Blanke et al. 2016 Journal of Cardiovascular Computed Tomography 10:491-499 (Year: 2016).*
Chandran, K.B., "Role of Computational Simulations in Heart Valve Dynamics and Design of Valvular Prostheses," Mar. 2010, Cardiovascular Engineering and Technology, 1(1), pp. 18-38 (30 pages).
Gessat, M. et al., "Image-Based Mechanical Analysis of Stent Deformation: Concept and Exemplary Implementation for Aortic Valve Stents," Jan. 2014, IEEE Transactions on Biomedical Engineering, vol. 61, No. 1, pp. 4-15 (12 pages).
Keefe, D.F. et al., "A Process for Design, Verification, Validation, and Manufacture of Medical Devices Using Immersive VR Environments," Nov. 3, 2010, Journal of Medical Devices, vol. 4 (7 pages).
Wang, Q. et al., "Patient-Specific Modeling of Biomechanical Interaction in Transcatheter Aortic Valve Deployment," Jul. 26, 2012, Journal of Biomechanics, 45(11) (19 pages).
International Search Report in International Application No. PCT/US17/55046, dated Jan. 16, 2018 (4 pages).
Written Opinion in International Application No. PCT/US17/55046, dated Jan. 16, 2018 (9 pages).
International Preliminary Report on Patentability in International Application No. PCT/US2017/055046, dated Apr. 9, 2019 (10 pages).
Extended European Search Report in European Patent Application No. 17874836.4, dated Apr. 8, 2020 (14 pages).
Blanke, Philipp et al., "Computed tomography assessment for transcatheter aortic valve in valve implantation: The Vancouver approach to predict anatomical risk for coronary obstruction and other considerations," Journal of Cardiovascular Computed Tomography, vol. 10, No. 6, Sep. 24, 2016, pp. 491-499 (9 pages).
Heitkemper, Megan et al., "Modeling risk of coronary obstruction during transcatheter aortic valve replacement," The Journal of Thoracic and Cardiovascular Surgery, vol. 159, No. 3, May 18, 2019 (13 pages).
Heitkemper, Megan et al., "Simple 2-dimensional anatomic model to predict the risk of coronary obstruction during transcatheter aortic valve replacement," Journal of Thoracic and Cardiovascular Surgery, Feb. 19, 2020 (12 pages).

* cited by examiner

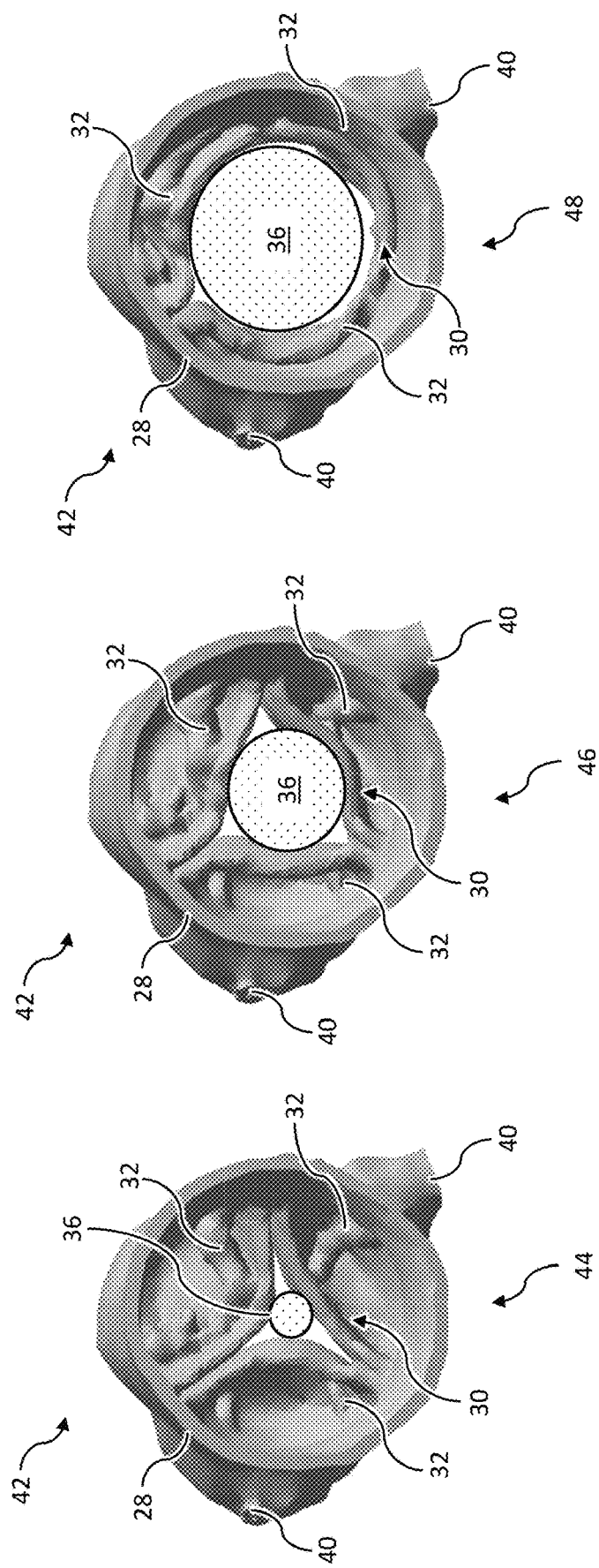

| | Right Coronary Artery | Left Coronary Artery |
|---|---|---|
| D: Potential Problem for RCA | 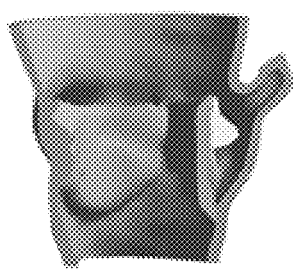 | 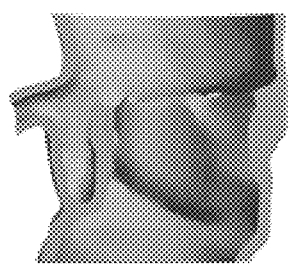 |
| E: Potential Problem for LCA |  | 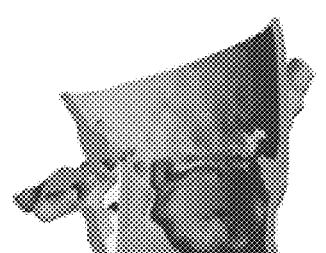 |
| F: Potential Problem for LCA | 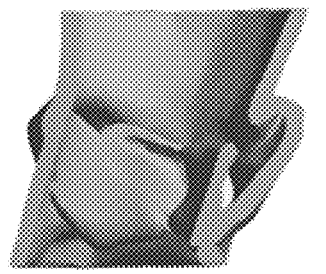 | 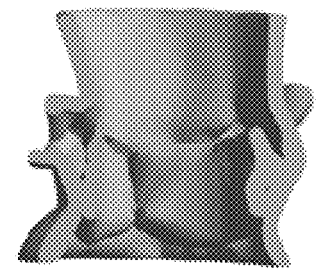 |
FIG. 32

| | Right Coronary Artery | Left Coronary Artery |
|---|---|---|
| G: Confirmed LCA Occlusion | 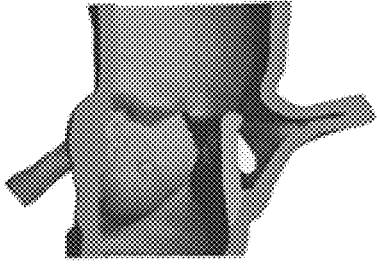 | 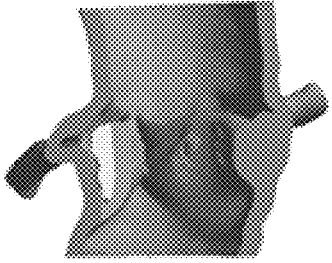 |
| H: Confirmed LCA Occlusion | 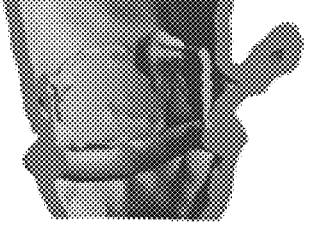 | 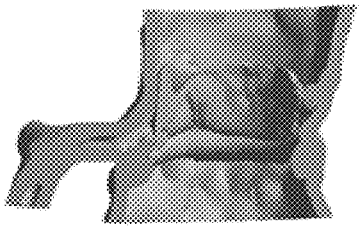 |
| I: Confirmed LCA Occlusion | 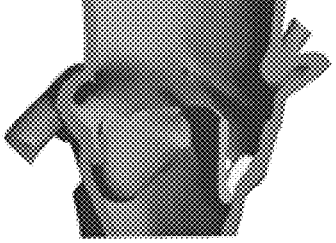 | 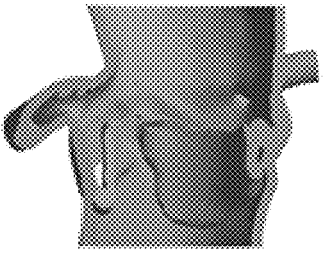 |
FIG. 33

SYSTEMS AND METHODS FOR PREDICTIVE HEART VALVE SIMULATION

CROSS-REFERENCED TO RELATED APPLICATIONS

This application is a National Stage of International Application No. PCT/US2017/055046, filed Oct. 4, 2017, entitled "SYSTEMS AND METHODS FOR PREDICTIVE HEART VALVE SIMULATION," which claims the benefit of U.S. Provisional Patent Application No. 62/403,940, filed on Oct. 4, 2016, entitled "SYSTEMS AND METHODS FOR PREDICTIVE HEART VALVE SIMULATION," the entire contents of which are incorporated herein by reference.

TECHNICAL FIELD

The present specification generally relates to systems and methods for predictive heart valve simulation.

BACKGROUND

Transcatheter aortic valve replacement (TAVR) can provide treatment for patients with severe aortic stenosis, and high-risk patients with various comorbidities, who cannot undergo conventional open-heart surgery. Despite the advantages associated with TAVR, complications such as, for example, conduction abnormalities, significant residual aortic regurgitation, and cerebrovascular events can still occur. In addition to the complications, life-threatening events can also occur during TAVR. The events can include coronary obstruction, paravalvular leakage, and thrombosis. Coronary obstruction can occur in either the right or left coronary artery. In some instances, coronary obstruction can be more prevalent with balloon expandable bioprostheses.

An average left coronary artery height and mean aortic root diameter can be used to identify criteria that can provide an indication that the patient is at risk for coronary obstruction. An average left coronary artery height and mean aortic root diameter can be approximately 10 millimeters (mm) and 28 mm, respectively. The identified criteria can include a coronary ostium height (basal leaflet insertion to coronary ostium distance) of less than 12 mm (or 10 mm), a sinus of Valsalva (SOV) diameter of less than 30 mm, a valve leaflet length greater than coronary height relative to an annulus, and a shallow SOV with bulky calcification The identified criteria can be used to determine if a patient should undergo coronary protection.

Existing criteria based approaches for providing an indication that a patient is at risk coronary obstruction fail to consider certain anatomic factors (e.g., lesion size and/or location, a sinus width at a coronary ostium, a leaflet's length, etc.). Moreover, existing criteria's in some instances cannot be individualized to the anatomy and conditions of the patient. Thus, existing criteria's for coronary obstruction fail to provide a sufficient relationship (e.g., detailed information on anatomical factors and their respective interrelationship relative to a coronary obstruction), and accuracy for guiding a clinical procedure decision making process.

SUMMARY

In an example, a method for predictive heart valve simulation can include generating anatomical model data based on image data characterizing anatomical regions of a heart of a patient. The anatomical model data can include three-dimensional shapes of the anatomical regions of the heart. The anatomical model data can be used by a geometric modeling engine to generate analytical model data. The analytical model data can include a three-dimensional mesh of the anatomical regions of the heart. The analytical model can be provided with a three-dimensional mesh of a surgical object. The analytical model data can be used by a numerical analysis engine to generate a deformed analytical model. The deformed analytical model can be indicative of a deformed position of the anatomical regions of the heart and a deformed position of the surgical object. The deformed analytical model can be evaluated to provide heart functionality measures for the heart.

In another example, a method for predictive heart valve simulation, can include segmenting, with one or more processors, anatomical regions of a heart of a patient from image data characterizing the heart of the patient. The anatomical regions can include one or more calcific nodules, an aortic root that can include a coronary artery, and an aortic leaflet. The image data of the one or more calcific nodules, the aortic root, and the aortic leaflet can be used by the one or more processors to generate anatomical model data. The anatomical model data can include three-dimensional shapes of the one or more calcific nodules, the aortic root, and the aortic leaflet. A deformed position of the aortic leaflet and the calcific nodule can be simulated by the one or more processors. A gap size can be quantified by the one or more processors based on the deformed position of the calcific nodule and the coronary artery of the aortic root.

In an even further example, a method for predictive heart valve simulation can include segmenting anatomical regions of a heart of a patient from image data characterizing the heart of the patient. The anatomical regions can include one or more calcific nodules, an aortic root that can include a coronary artery, and an aortic leaflet. The image data of the one or more calcific nodules, the aortic root, and the aortic leaflet can be used by an image processing engine to generate anatomical model data. The anatomical model data can include three-dimensional shapes of the one or more calcific nodules, the aortic root, and the aortic leaflet. The anatomical model data can be used by a geometric modeling engine to generate analytical model data. The analytical model data can include three-dimensional meshes of the one or more calcific nodules, the aortic root, and the aortic leaflet. The analytical model data can be used by a numerical analysis engine to generate a deformed analytical model. The deformed analytical model can be indicative of a deformed position of the calcific nodule and the coronary artery of the aortic root. A gap size can be determined between the deformed position of the calcific nodule and the coronary artery of the aortic root.

In another example, a method for predictive heart valve simulation can include receiving image data indicative of a heart of a patient. The image data can include a calcific nodule, an aortic root that can include a coronary artery, and an aortic leaflet. One or more parameters can be determined based on the anatomical model data. The one or more model parameters can include a thickness t of the calcific nodule. A deformed position of the aortic leaflet and the calcific nodule can be determined by a parametric analysis engine based on the one or more model parameters. The parametric analysis engine can be programmed to model the aortic leaflet in a fully expanded position. A gap size can be quantified with the parametric analysis engine based on the deformed position of the calcific nodule and the coronary artery of the aortic root. The gap size can correspond to a two-dimensional distance between a nodule point on the deformed position of the calcific nodule and an ostium point on the coronary artery of the aortic root.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 10-14 illustrate exemplary deformed analytical models.

FIGS. 31-33 illustrate exemplary deformed analytical models collected during the patient study.

DETAILED DESCRIPTION

Systems and methods are described herein for evaluating anatomic factors of patients. The anatomic factors can be evaluated according to the systems and methods described herein based on image data. For example, anatomic parameters such as calcium nodule size and location can be used to predict coronary obstruction. Moreover, the systems and methods described herein can be used as a framework to quantify coronary obstruction prior to a procedure, such as transcatheter aortic valve replacement (TAVR). It is noted that, while the examples described herein are with reference to TAVR, the examples described herein should not be construed as limited to only TAVR. The examples described herein can be used to predict outcomes or risks associated with Transcatheter Mitral Valve Replacement (TMVR), or any other existing or yet to be developed transcatheter valve replacement or insertion procedure. Exemplary procedures can include, but not limited to, transcatheter valve replacement or insertion in a pulmonary root, pulmonary vein ostium, tricuspid annulus, superior vena cava, or inferior vena cava.

Figure 1:
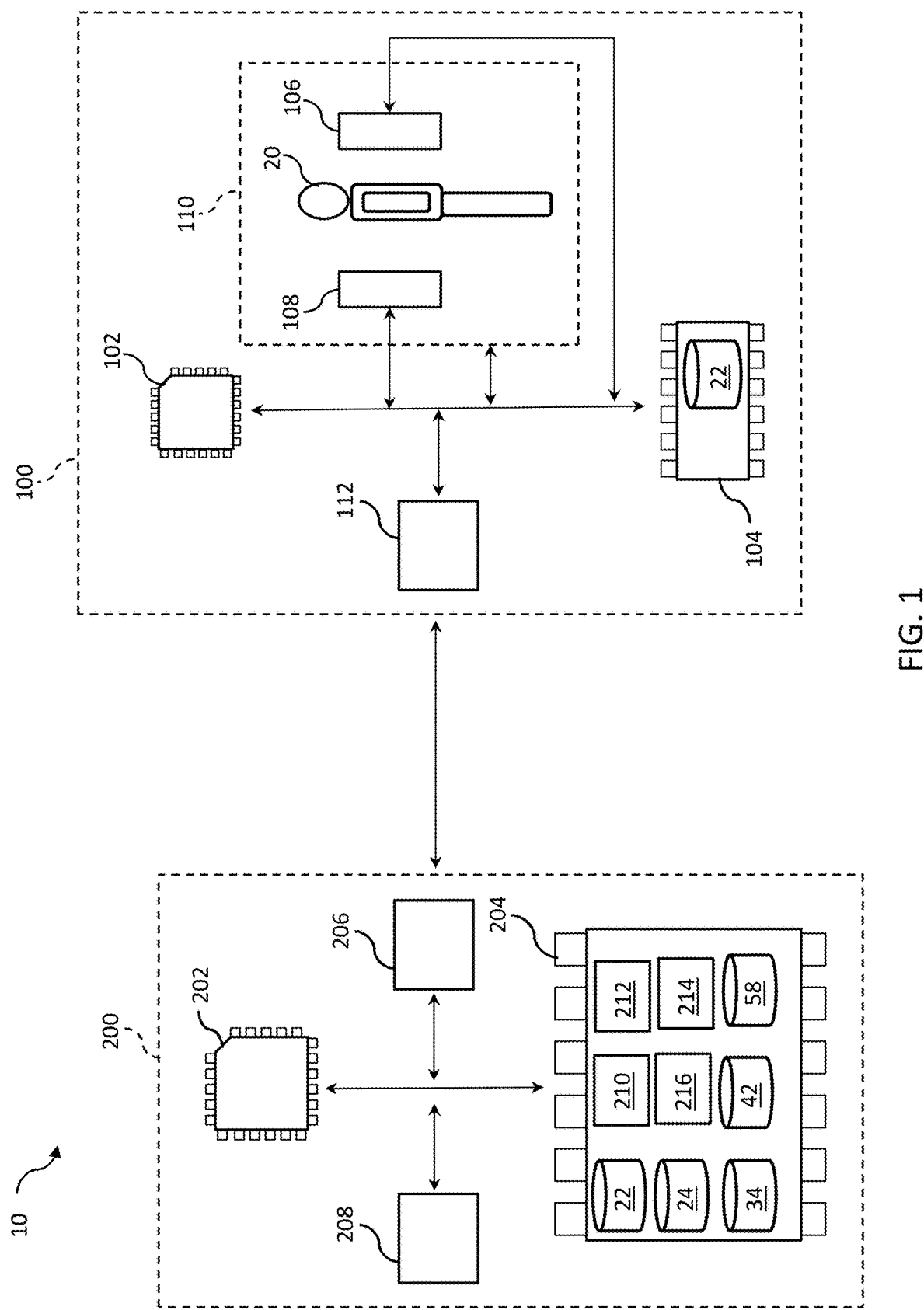
FIG. 1 illustrates an example of a system for predictive heart valve simulation.

FIG. 1 relates to a system 10 for predictive heart valve simulation. The system 10 can be configured to collect image data characterizing a heart of a patient 20. The system 10 can include an imaging device 100. The imaging device 100 can be configured to college image data 22 in two or three dimensions of the patient. The image data 22 can include, but not limited to, X-ray image data (e.g., X-ray computed tomography (CT) images), magnetic resonance imaging (MRI) image data, or ultrasound image data. An imaging device 100, as described herein, can correspond to any modality that can be configured to collect image data 22 of the patient 20, such as the patient's heart.

The imaging device 100 can further include one or more processors 102 for executing machine readable instructions and memory 104 for storing the machine readable instructions. The one or more processors 102 can be coupled to the memory 104, and configured to retrieve the stored machine readable instructions at the memory 104. The one or more processors 102 can include an integrated circuit, a microchip, a computer, or any other computing device capable of executing machine readable instructions. The memory 104 can include RAM, ROM, a flash memory, a hard drive, or any device capable of storing machine readable instructions.

The imaging device 100 can further include a sensor 106. The sensor 106 can be configured to collect measurements of the heart of the patient 20. The sensor 106 can be coupled to the one or more processors 102, the memory 104, or both. It is noted that the term "sensor," as used herein, corresponds to a device that can be configured to measure a physical quantity and convert the measured physical quantity into a representative signal, which can be correlated to a measured value of the physical quantity. In some examples, the imaging device 100 can include an X-ray CT system for collecting X-ray data. Accordingly, the sensor 106 can be an X-ray detector, and can be configured to detect photons such as, for example, a point detector, a linear detector, or a planar detector.

In some examples, the imaging device 100 can include a source 108. The source 108 can be configured to generate excitation energy that can be detectable by the sensor 106. The source 108 can be coupled to the one or more processors 102, the memory 104, or both. In examples where the imaging device 100 includes an X-ray CT system, the source 108 can be an X-ray source. The X-ray can be configured to emit photons along a path. The path can begin at the source 108 and terminate at the sensor 106. The heart of the patient 20 can be located along the path, and thus between the source 108 and the sensor 106. A portion of the photons can be absorbed by the patient 20, while measurements are collected by the sensor 106. Accordingly, the photons received by the sensor 106 can be indicative of the patient 20, e.g., the intensity of the photons can be correlated to the density of patient's 20 body.

The imaging device 100 can further include an actuation assembly 110. The actuation assembly 110 can be configured to manipulate the patient 20, the sensor 106, the source 108, or a combination thereof. For example, the actuation assembly 110 can include one or more servo-mechanisms that can be configured to control an amount of force required for manipulating the patient 20, the sensor 106, the source 108, or a combination thereof. In the examples described herein, the one or more processors 102, the memory 104, or both can be integral with any or all of the sensor 106, the source 108, and the actuation assembly 110. However, it is to be understood that the one or more processors 102, the memory 104, or both, can be separate components that can be coupled with one another.

In some examples, the actuation assembly 110 can include a mechanical actuator, a hydraulic actuator, a pneumatic actuator, an electrical actuator, or a combination thereof. The actuation assembly 110 can be coupled to the one or more processors 102, the memory 104, or both. The one or more processors 102 can be configured to execute the machine readable instructions to control the operation of the sensor 106, the source 108, and the actuation assembly 110. The actuation assembly 110 can be configured to cause relative motion of the patient 20 with respect to the sensor 106 and the source 108. For example, the actuation assembly 110 can include a gantry system for moving the sensor 106 and the source 108 in a substantially circular pattern relative the patient 20.

In examples where the imaging device 100 includes an X-ray CT system, multiple measurements of the patient 20 can be collected by the sensor 106, relative motion between the patient 20 and the sensor 106, the source 108, or both. Each measurement can be constructed into an image having greater dimensional complexity than the measurement generated by the sensor 106. For example, each measurement can be indicative of absorption or density of the patient 20, and can be constructed into the image data 22 indicative of the anatomy of the patient 20. For example, measurements collected by a line detector can be used to produce a two-dimensional images showing a slice of the patient's anatomy. A plurality of slices can be combined to provide a full representation of the patient 20 in three-dimensions such as, for example, by combining slices collected along a direction orthogonal to the plane of the slices. Measurements collected by a planar detector can be combined into three-dimensional images of the patient 20.

The imaging device 100 can further include network interface hardware 112. The network interface hardware can be coupled to the one or more processors 102 such that the imaging device 100 can be coupled to another device via a network. The network can include, but not limited to, a wide area network (WAN), a local area network (LAN), a personal area network (PAN), or a combination thereof. The network interface hardware 112 can be configured to communicate (e.g., send and/or receive data signals) via any wired or wireless communication protocol. For example, the network interface hardware 112 can include an antenna, a modem, LAN port, wireless fidelity (Wi-Fi) card, WiMax card, near-field communication hardware, or the like. Accordingly, the imaging device 100 can be coupled to a network via wires, a WAN, a LAN, a PAN, or the like.

Suitable LANs can include, but not limited to, wired Ethernet and/or wireless technologies such as, for example, Wi-Fi. Suitable PANs can include, but not limited to, wireless technologies such as, for example, infrared data association (IrDA), BLUETOOTH, wireless universal serial bus (USB), Z-WAVE, ZIGBEE, or the like. Alternatively or additionally, suitable PANs can further include, but not limited to, wired computer buses such as, for example, USB and FIREWIRE. Thus, any components of the imaging device 100 can utilize one or more network components to communicate data via the network.

The system 10 can further include an image analysis device 200. The image analysis device can be configured to executing machine readable instructions to provide image analysis and anatomical simulation functionality based on anatomical information extracted from the image data 22. The image analysis device 200 can include one or more processors 202. The one or more processors 202 can be configured to retrieve and execute the machine readable instruction stored in memory 204. The one or more processors 202 can be coupled to network interface hardware 206. It is noted that, while the image analysis device 200 is illustrated in the example of FIG. 1 as being a single machine, each of the one or more processors 202, the memory 204, and the network interface hardware 206, including their components and functions, can be distributed amongst a plurality of machines that can be communicatively coupled to one another. Additionally, it is noted that in some examples, the image analysis device 200 and the imaging device 100 can be implemented on a single machine. The image analysis device 200 can further include a display 208. The display 208 can be coupled to the one or more processors 202. Alternatively or additionally, the display can be provided as a wearable device, such as, for example a smart watch or a virtual reality headset. Suitable example of virtual reality headsets can include Samsung Gear VR, Sony PlayStation VR, Oculus Rift, or the like.

Figure 3:
FIG. 3 illustrates exemplary image data.
Figure 15:
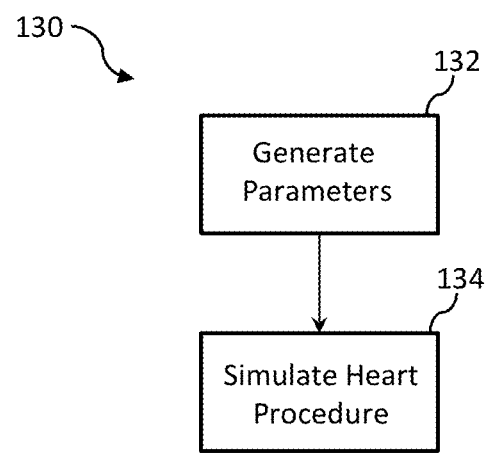
FIG. 15 illustrates an example of a method for predictive heart valve simulation.
Figure 17:
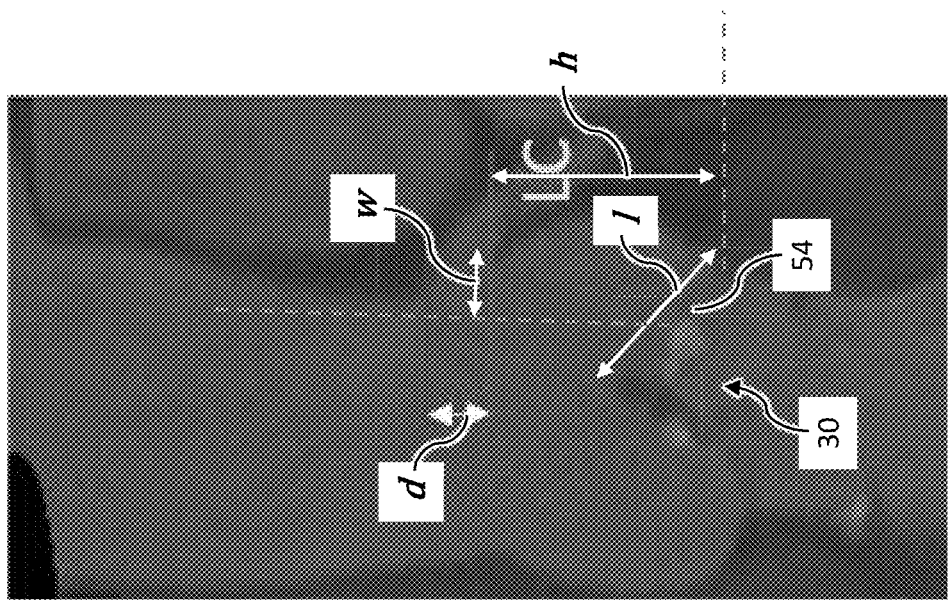
FIGS. 16-19 illustrate an example of slices of computed tomography (CT).
Figure 16:
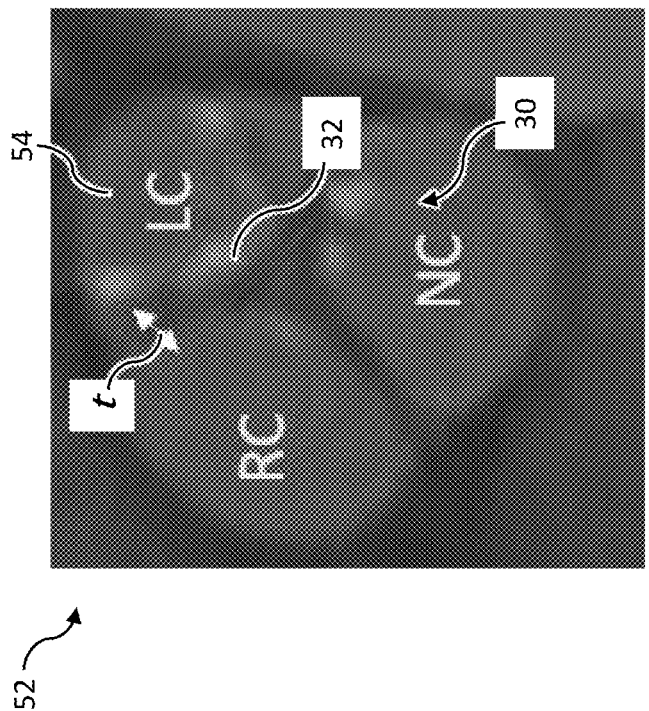
Figure 19:
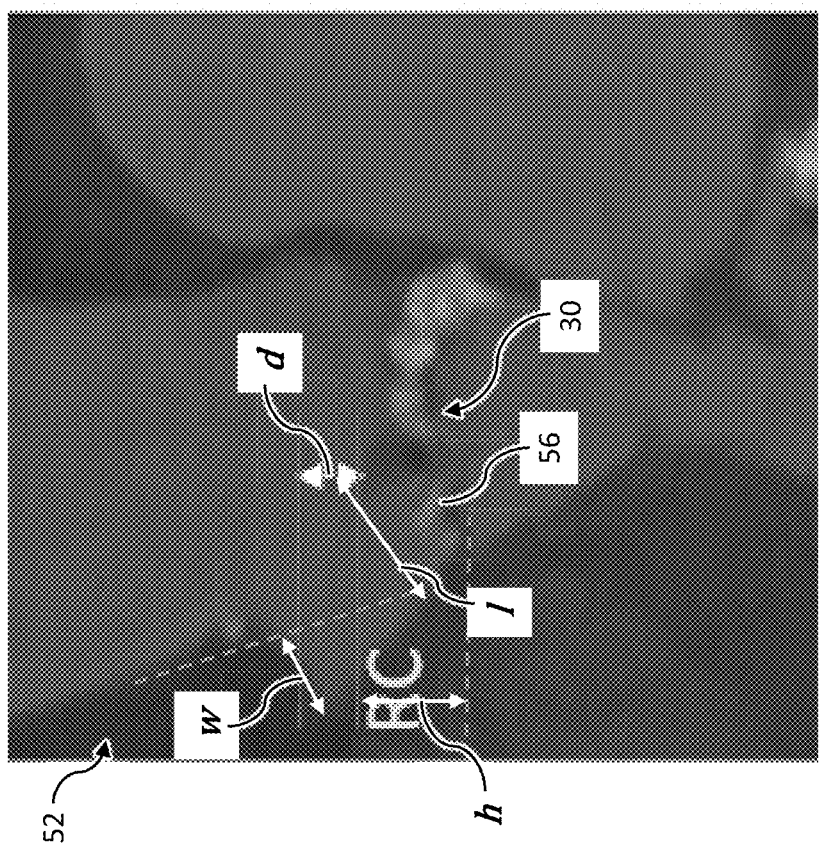
Figure 18:
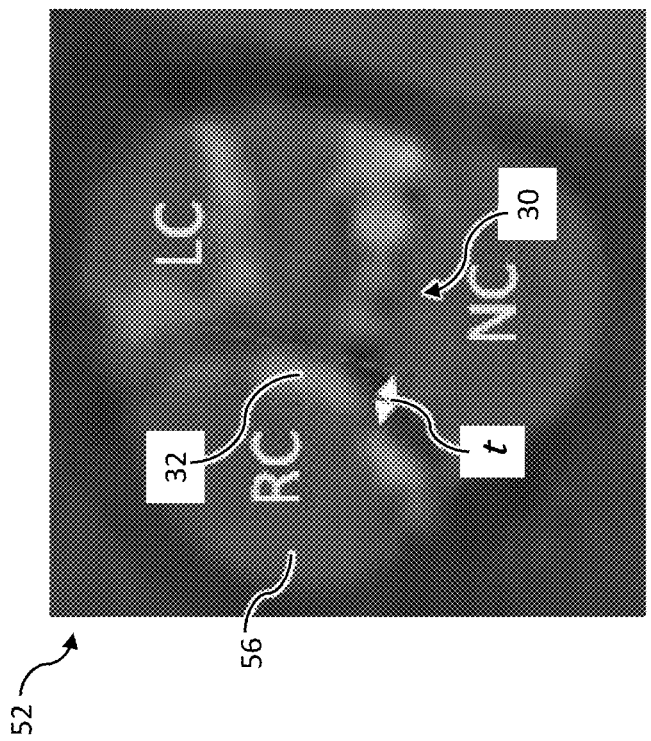
Figure 20:
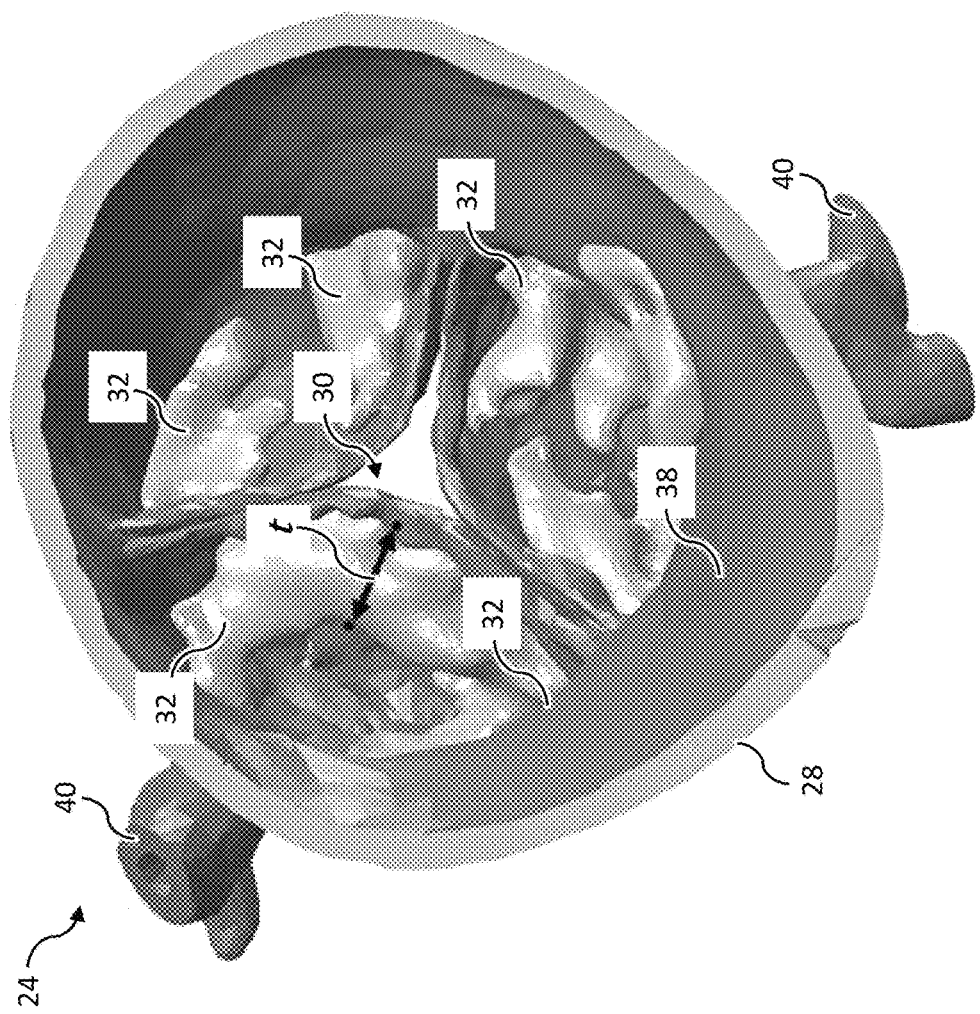
FIGS. 20-21 illustrate exemplary analytical model data.
Figure 24:
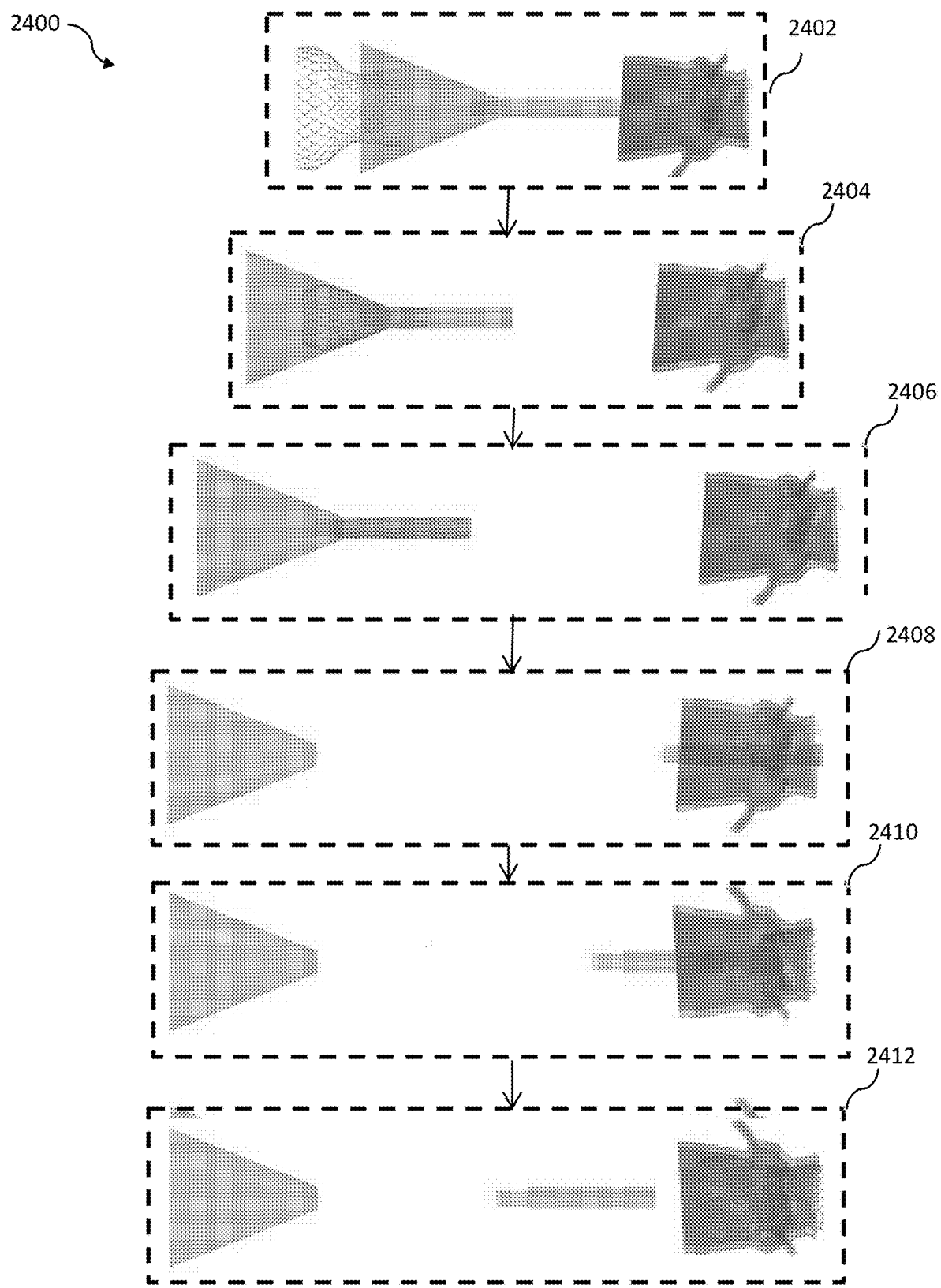
FIG. 24 illustrates an example of a method for delivery of a self-expandable stent to a patient.

In view of the foregoing structural and functional features described above, a method that can be implemented will be better appreciated with reference to FIGS. 3, 15, and 24. While, for purposes of simplicity of explanation, the method of FIGS. 3, 15, and 24 are shown and described as executing serially, it is to be understood and appreciated that such method is not limited by the illustrated order, as some aspects could, in other examples, occur in different orders and/or concurrently with other aspects from that shown and described herein. Moreover, not all illustrated features may be required to implement a method. The method or portions thereof can be implemented as instructions stored in one or more non-transitory storage media as well as be executed by a processing resource (e.g., one or more processor) of a system, for example, the image analysis device 200.

Figure 2:
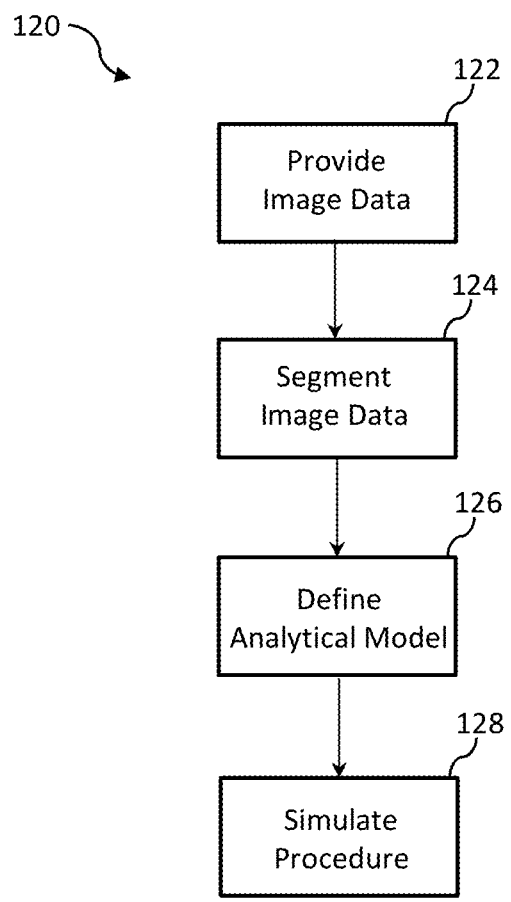
FIG. 2 illustrates an example of a method for predictive heart valve simulation.

FIG. 2 illustrates an example of a flow diagram illustrating an example method 120 for predictive heart valve simulation. The method 120 can include a process 122 for providing image data 22. In some examples, the image data 22 can include X-ray CT image data collected based on the patient 20. The image data 22 can be collected prior to a clinical procedure. For example, prior to performing a heart procedure (e.g., TAVR), the image data 22 can be generated based on the patient 20, which, as described herein, can be used to predict the outcome or risks associated with the clinical procedure. The image data 22 can characterize an anatomical region of the patient 20. The anatomical region can include one or more of the pulmonary root, pulmonary vein ostium, tricuspid annulus, superior vena cava, or inferior vena cava.

The image data 22 can be stored in the memory 104 of the imaging device 104. In some examples, the image data 22 can be organized such as, for example, into systole data and/or diastole data. The image data 22 can be transmitted to the memory 204 of the image analysis device 200 such as, for example, via the network interface hardware 112 and the network interface hardware 206. Additionally, the image data 22 can be stored on or transmitted via an intermediary device that can include memory such as, for example, a cloud storage device or a portable memory.

Figure 4:
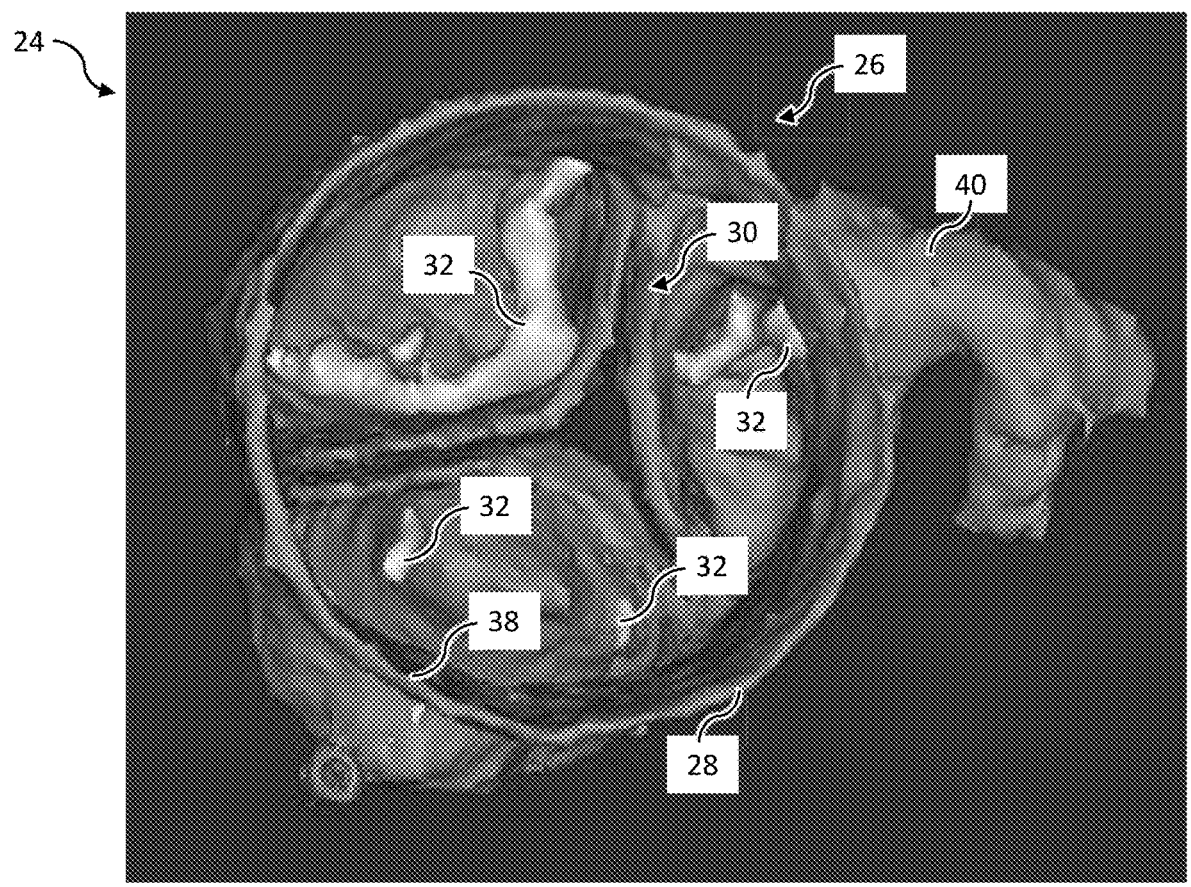
FIG. 4 illustrates exemplary anatomical model data.
Figure 5:
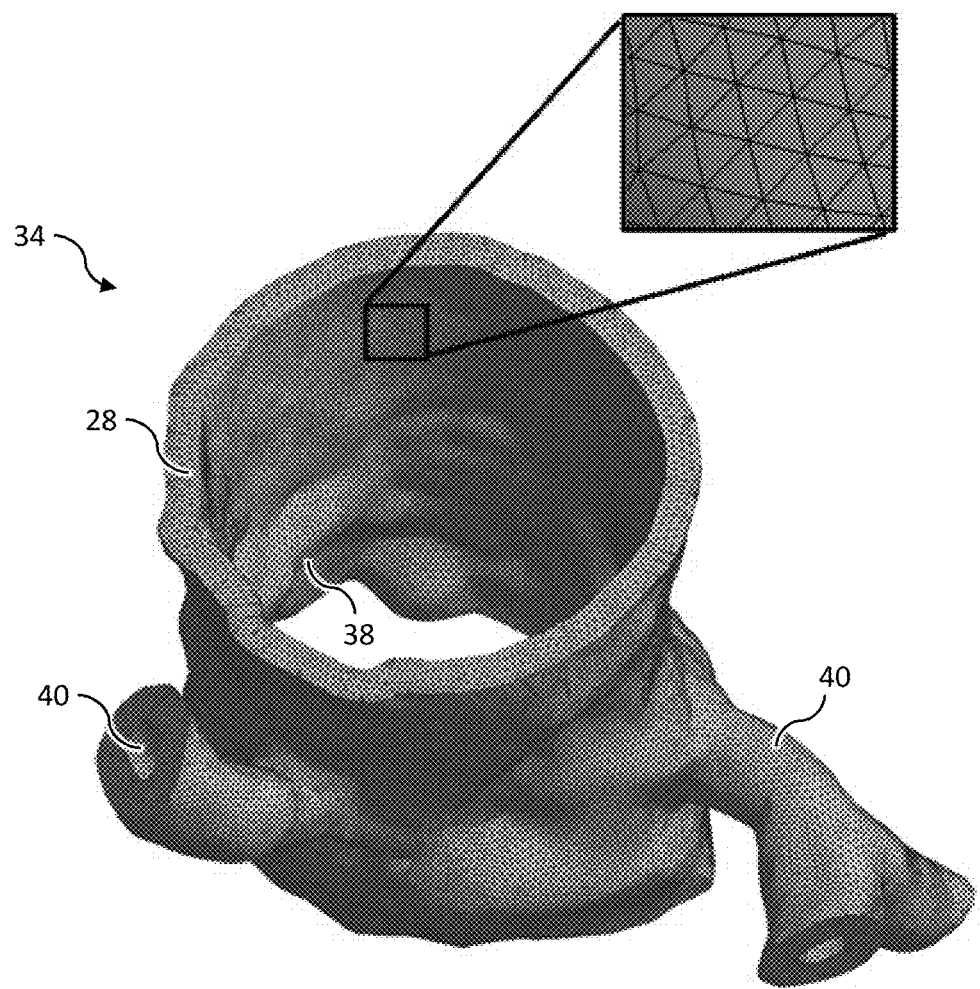
FIGS. 5-9 illustrate exemplary analytical model data.
Figure 6:
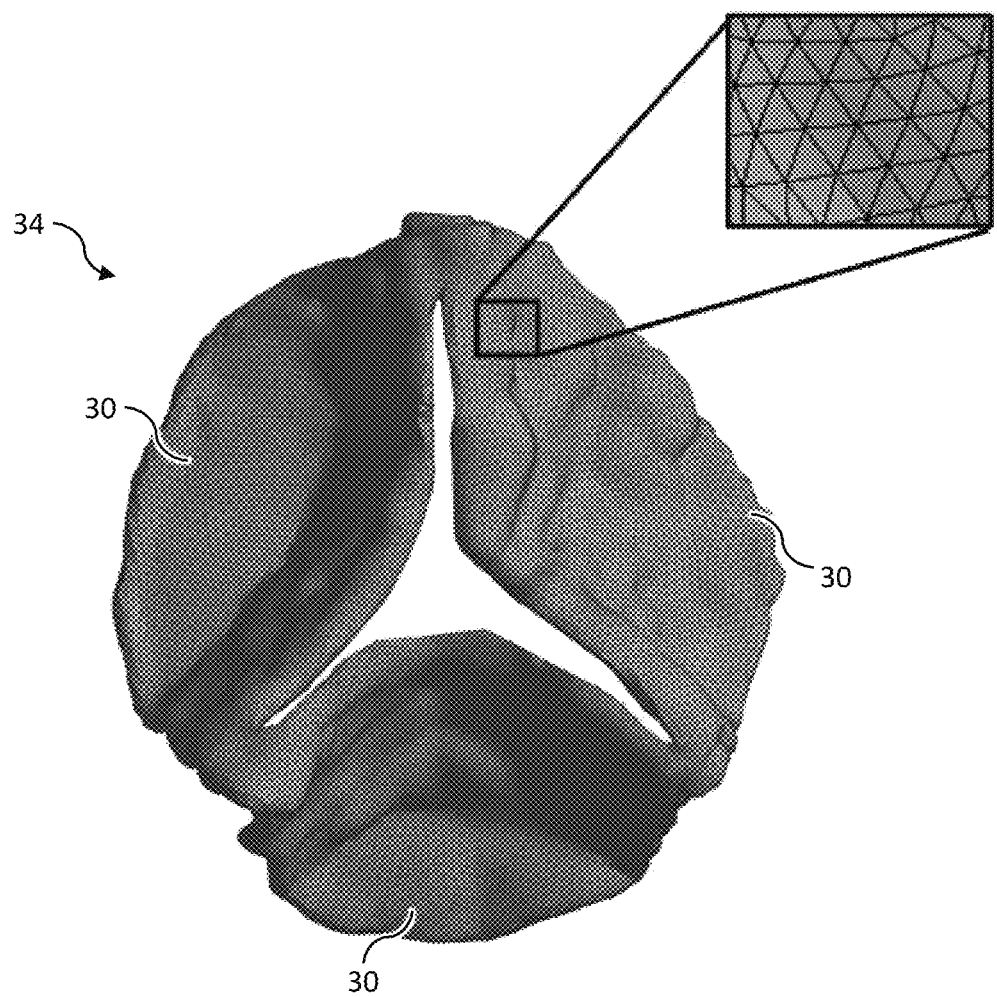
Figure 7:
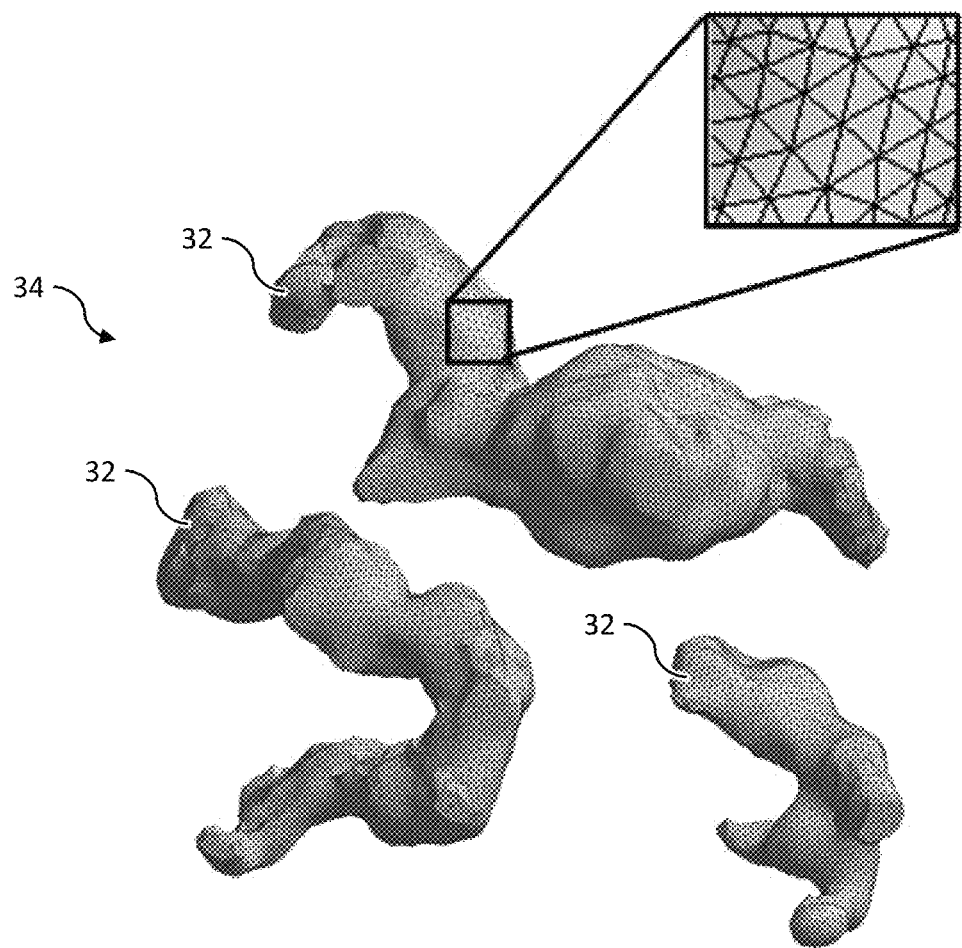

The method 120 can further include a process 124 for segmenting the image data 22. At process 124, the image data 22 can be used to generate anatomical model data 24, such as shown in FIG. 4. The anatomical model data 24 can include computer-aided design (CAD) shapes composed of points, curves, surfaces, solids, or the like encoded into a machine readable format. In some examples, the image analysis device 200 can execute an image processing engine 210 provided on the memory 204. The image processing engine 210 can be programmed to generate the anatomical model data 24 based on the image data 22. The anatomical model data 24 can be provided in two-dimensions or three-dimensions. For example, CT images can include pixels or voxels indicative of relative intensity that can be encoded into a machine readable format such as, for example, Digital Imaging and Communications in Medicine (DICOM) format, X-ray, raw image data, or the like. Accordingly, the image processing engine 210 can include image processing methods that can evaluate CT images. Suitable commercial software toolkits including image processing methods are available such as, but not limited to, RadiAnt™, available from Medixant, and Mimics available from Materialise.

At process 124, the image processing engine 210 can be further programmed to segment image data characterizing one or more anatomical regions 26 from the image data 22. The imaging processing engine 210 can be programmed to generate the anatomical model data 24 based on the segmented image data. For example, the anatomical regions 26 can include anatomy of the patient 10 that can be manipulated during a clinical procedure. In the example of TAVR, the anatomical regions 26 can include an aortic root 28, native aortic leaflets 30, and calcific nodules 32. The calcific nodules 32 can correspond to calcium based deposits that can develop within the patient 20. The calcific nodules 32 can have an irregular geometric shape and can vary in size and shape for each patient 20. The segmentation can make use of various algorithms such as, for example, thresholding, edge detection, shape recognition, filtering, clustering, or the like. For example, the anatomical regions 26 of CT images can include different ranges of intensity (e.g., pixel or voxel) relative to tissue stiffness. Once segmented, each of the anatomical regions 26 can be transformed into a CAD shape within the anatomical model data 24.

Figure 8B:
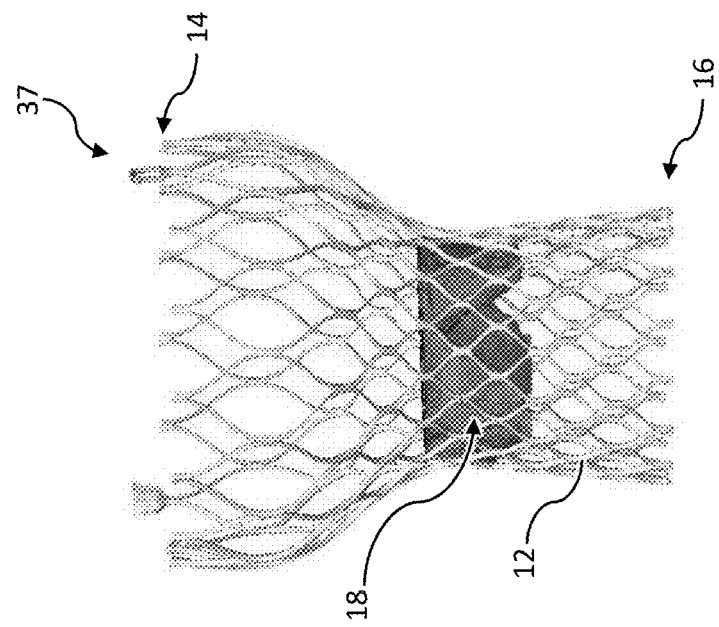
Figure 8A:
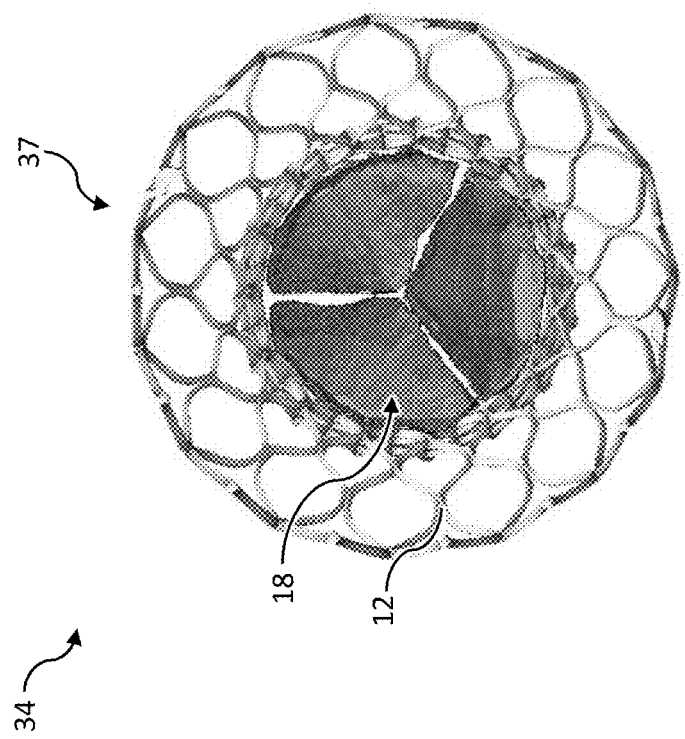
Figure 9:
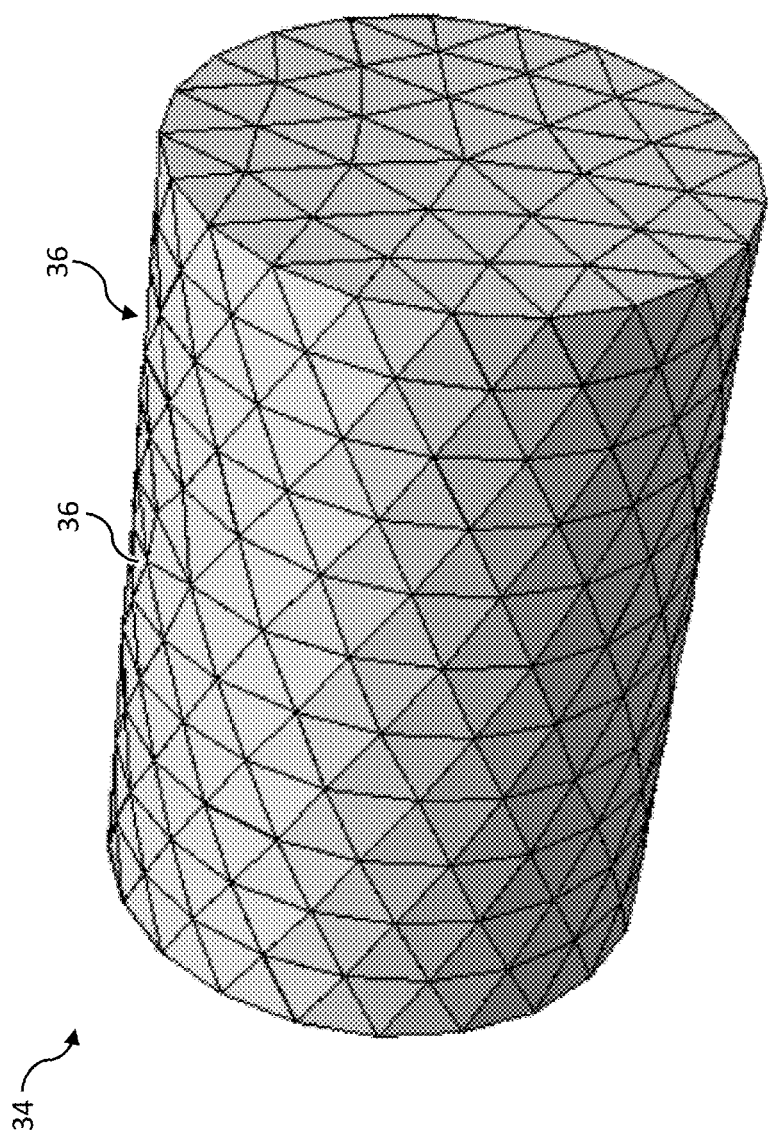

The method 120 can further include a process 124 for defining analytical model data 34, such as shown in FIGS. 5, 6, 7, 8A, 8B, and 9. Generally, the analytical model data 34 can include mesh elements such as, for example, nodes and edges, that can be used for numerical analysis. In some examples, the image analysis device 200 can be configured to execute a geometric modeling engine 212 provided on the memory 204. The geometric modeling engine 212 can be programmed to generate analytical model data 34 based on the anatomical model data 24. Alternatively or additionally, the analytical model data 34 can include a surgical object 36 representative of model implants, surgical instruments, or any other device that can interact with the anatomical regions 26 of the patient 20 during the clinical procedure. For example, the surgical objects 36 can include a three-dimensional model of a transcatheter aortic valve (TAV) 37, such as shown in FIGS. 8A and 8B. The TAV 37 can include a stent 12 that can be configured to extend between a top portion 14 and a bottom portion 16 of the TAV 37. The stent 12 can include artificial leaflets 18. Additionally, or alternatively, the TAV 37 can be modeled by a correspondingly shaped cylinder 39. Suitable commercial software toolkits for implementing the geometric modeling engine 212 can include, but not limited to, SolidWorks®.

In the example of TAVR, the analytical model data 34 can include meshes. The meshes can correspond to each of the aortic root 28, the aortic leaflets 30, the calcific nodules 32, and the surgical object 36. The meshes can be mapped to the CAD shapes of the anatomical regions 26 and the surgical objects 36. For example, the nodes can be mapped to curves, surfaces, points, or the like of the anatomical model data 24. The nodes and edges of the mesh can be formed in a variety of shapes such as, for example, triangle, quadrilateral, tetrahedron, pyramid, hexahedron, or the like. In a test example, 10-node tetrahedral elements were mapped with a patch-independent algorithm to the anatomical regions 26 corresponding to soft tissue regions. The stent 12 was meshed using hexahedron elements. The total number of mesh elements varied for each patient, and was a function of the shape and size of the anatomical regions 26 (e.g., aortic wall 38, aortic leaflets 30, coronary arteries 40, and calcific nodules 32).

The method 120 can further include a process 128 for simulating the clinical procedure. In some examples, the image analysis device 200 can be configured to execute a numerical analysis engine 214 provided on the memory 204. The numerical analysis engine 214 can be programmed to map boundary conditions, and a system of equations to the analytical model data 34. The numerical analysis engine 214 can be programmed to solve the system of equations based on the boundary conditions to simulate the clinical procedure. For example, the numerical analysis engine 214 can be programmed for finite element analysis (FEA), computational fluid dynamics (CFD), or the like. Suitable commercial software toolkits for implementing the numerical analysis engine 214 can include, but not limited to, ANSYS® available from ANSYS, Inc.

The numerical analysis engine 214 can be programmed to simulate the clinical procedure by assigning boundary conditions to the analytical model data 34 and manipulating the surgical objects 36 to resemble the clinical procedure. In the example of TAVR, the numerical analysis engine 214 can be programmed to model an impact of the clinical procedure upon the anatomy of the patient 20. For example, the movement aortic leaflets 30 and the calcific nodules 32 can be modeled by the numerical analysis engine 204 to quantify an amount of coronary obstruction, paravalvular leakage, thrombosis, or a combination thereof. The material properties of the aortic root 28 and the aortic leaflets 30 can be considered to be linear elastic, and the calcific nodules 32 and can be modeled by the numerical analysis engine 204 as rigid objects. The physical characteristics of the aortic root 28 and the aortic leaflets 30 can be mapped to the analytical model data 34, e.g., the mesh can be assigned a Young's modulus of about 2,000 kilopascal (kPa), Poisson's ratio of about 0.495, and a density of about 1,000 kilograms per meter squared ($Kg/m^3$). Moreover, the surgical object 36 can be modeled by the numerical analysis engine 204 as the stent 12, the TAV 37, the cylinder 39, or the like. For example, the surgical object 36 can be modeled by the numerical analysis engine 204 as homogeneous isotropic stainless steel with a Young's modulus of about 205 gigapascal (GPa), Poisson ratio of about 0.275, and tensile strength of about 620 megapascals (MPa).

A pessimistic scenario can be modeled by considering deformation of the aortic leaflets 30 in a fully expanded position. In some examples, the pessimistic scenario can be simulated by representing the TAV 37 as the cylinder 39 that expands in the analytical model data 34 (e.g., the surgical object 36 can be a cylinder 39 with expanding dimensions). It is noted that more complex scenarios can be modeled by representing the TAV 37 with a less idealized model without departing from the examples described herein. In some examples, the surgical object 36 can include a model of the TAV 37, which can be expanded in a manner that imitates a physical deployment (e.g., dimensions, force, rate of change) of the TAV 37 (e.g., a self-expanding device or a balloon-expanding device). The surgical object 36 can be deployed at a center of the commissures to expand the aortic leaflets 30. Since a contact coefficient between the stent 12 and aortic leaflets 30 is not well known, a frictionless contact can be specified. Alternatively, the contact coefficient can be specified. In addition, for better convergence, a "Normal Lagrange" formulation and "Adjust to Touch" interface treatment can be used at a contact region. To account for a nonlinearity of the problem, a sparse direct solver with full Newton-Raphson control can be used. A displacement control boundary condition can be applied to the surgical object 36 based on an annulus diameter of the aortic root 28.

The numerical analysis engine 214 can be further programmed to generate a deformed analytical model 42 by modeling the impact of changing the dimensions of the surgical object 36. For example, as the dimensions of the surgical object 36 change, the position of aortic leaflets 30 and the calcific nodules 32 can respond by changing position (e.g., the aortic leaflets 30 can expand radially to cause the calcific nodules 32 attached thereto to change position). Likewise, the surgical object 36 can deform in response to interaction with the aortic leaflets 30 and the calcific nodules 32. Accordingly, each deformed analytical model 42 can correspond to a deformed position of the aortic leaflets 30, the calcific nodules 32, the surgical object 36 caused by the TAVR. Any number of deformed analytical models 42 can be defined to model an initial deployment 44 of the surgical object 36, such as shown in FIG. 10, an intermediate deployment of the surgical object 36, such as shown in FIG. 11, a full deployment 48 of the surgical object 36, such as shown in FIGS. 12A and 12B, and any position there between.

In some examples, the surgical object 36 can be changed in the analytical model data 34 to generate additional deformed analytical models 42. Accordingly, the numerical analysis engine 214 can be programmed to predict the impact of the use of different sizes or types of TAV's 37 upon the anatomy of the patient 20. Moreover, the surgical object 36 can be repositioned in the analytical model data 34 to determine the impact of changes in positioning upon the deformed analytical models 42. For example, the TAV 37 can have an insertion depth 60 (e.g., a distance between the top portion 14 of the TAV 37 and the annulus 62 of the aortic root 28). Additionally, a pitch angle and yaw angle relative to a centerline 64 of the aortic root 28 can be modeled by the numerical analysis engine 214. Accordingly, the pitch angle, yaw angle, insertion depth 60, or a combination thereof, can be modeled to quantify a sensitivity of the patient 20 to the TAVR. In some examples, deformed analytical models 42 can be generated consecutively, or in parallel, to allow for direct comparison of different sizes, types, or positions of TAV's 37. For example, each of the deformed analytical models 42 can be depicted on the display 208. Thus, an efficacy of each TAV 37 can be visualized prior to the clinical procedure, for example, prior to performing TAVR.

Figure 12B:
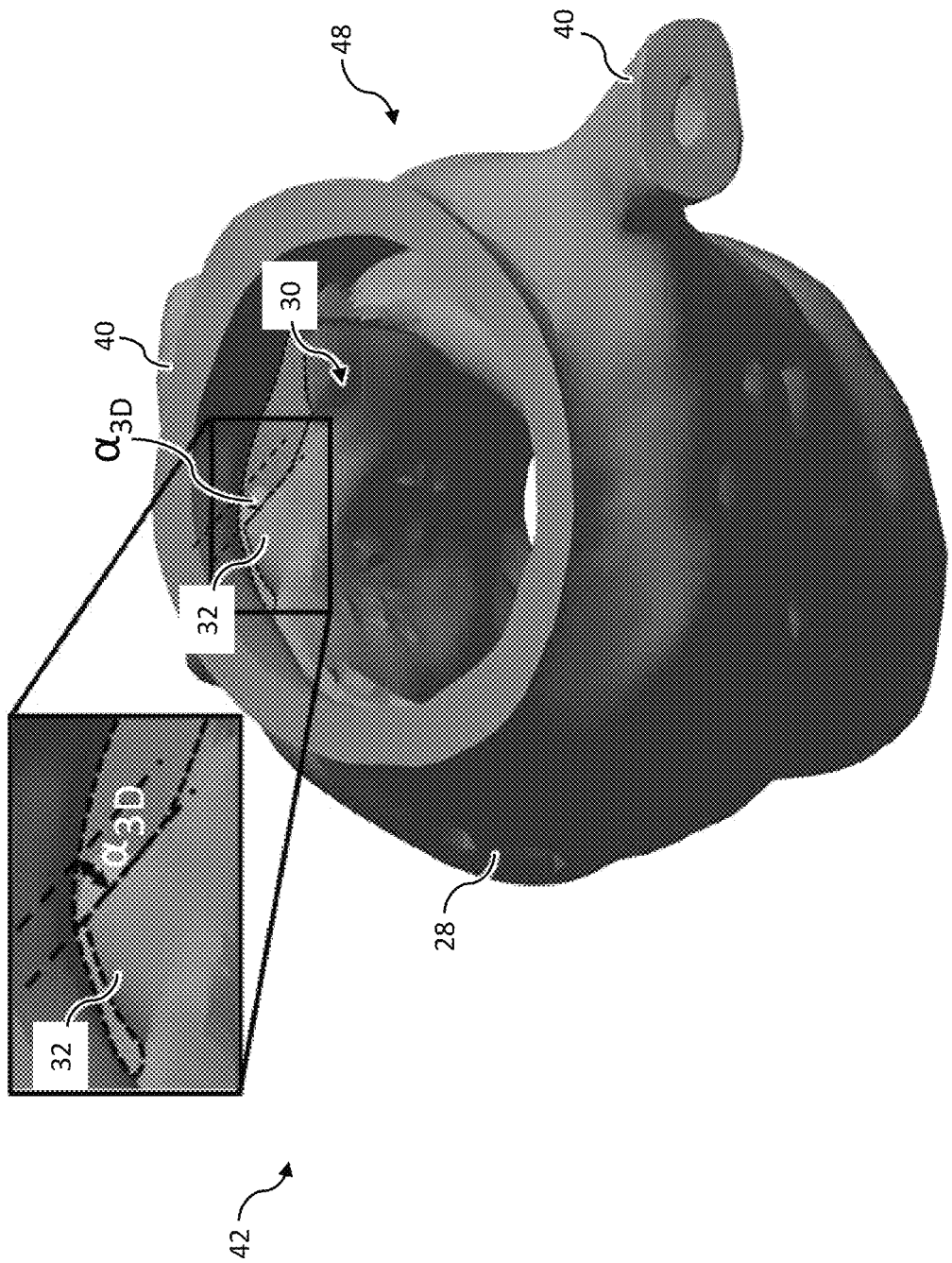

Referring collectively to FIGS. 12A and 12B, after modeling the deformation of the aortic leaflets 30 caused by full deployment 48 of the surgical object 36, a gap size $\alpha_{3D}$ can be determined. The gap size $\alpha_{3D}$ can correspond to a shortest three-dimensional distance between a coronary ostium of the coronary artery 40 and a potential obstruction such as, for example, a calcific nodule 32 on the aortic leaflets 30, or the aortic leaflets 30. Thus, the gap size $\alpha_{3D}$ can be determined based on a position of the aortic leaflets 30 after TAV stent deployment. The gap size $\alpha_{3D}$ can be correlated to risk of coronary obstruction. For proper heart function, blood travels over the aortic leaflets 32 to reach the coronary ostium. During TAV stent deployment, aortic leaflets 32 can be forced towards the coronary arteries 40 to accommodate the new valve prosthesis. A life-threatening complication known as coronary ostium obstruction can occur when the aortic leaflets 32 are forced into a position that blocks the coronary ostia, cutting off blood flow to remaining portions of the heart.

Accordingly, a small gap size $\alpha_{3D}$ (e.g., less than about 3 millimeters (mm)) can provide an indication that the coronary artery 40 is blocked. Moreover, it is noted that for some patients, the gap size $\alpha_{3D}$ can be measured relatively easily. However, for other patients, especially those at high risk for coronary obstruction, additional views and inspection can be required to determine the gap size $\alpha_{3D}$. Accordingly, the deformed analytical model 42 can improve an accuracy of the diagnosis by providing a full three-dimensional geometric representation of the calcific nodule 32, the aortic leaflets 32, and the coronary artery 40.

Referring collectively to FIGS. 8A, 8B, 12A and 12B, after modeling the deformation of the aortic leaflets 30 caused by full deployment 48 of the surgical object 36, a gap size can be determined to quantify paravalvular leakage (e.g., undesired blood flow between the TAV 37 and the annulus of the aortic root 28). The gap size can correspond to a largest three-dimensional distance between the stent 12 or artificial leaflets 18 relative to the annulus of the aortic root 28. Generally, the gap size can be correlated to risk of paravalvular leakage.

Figure 13:
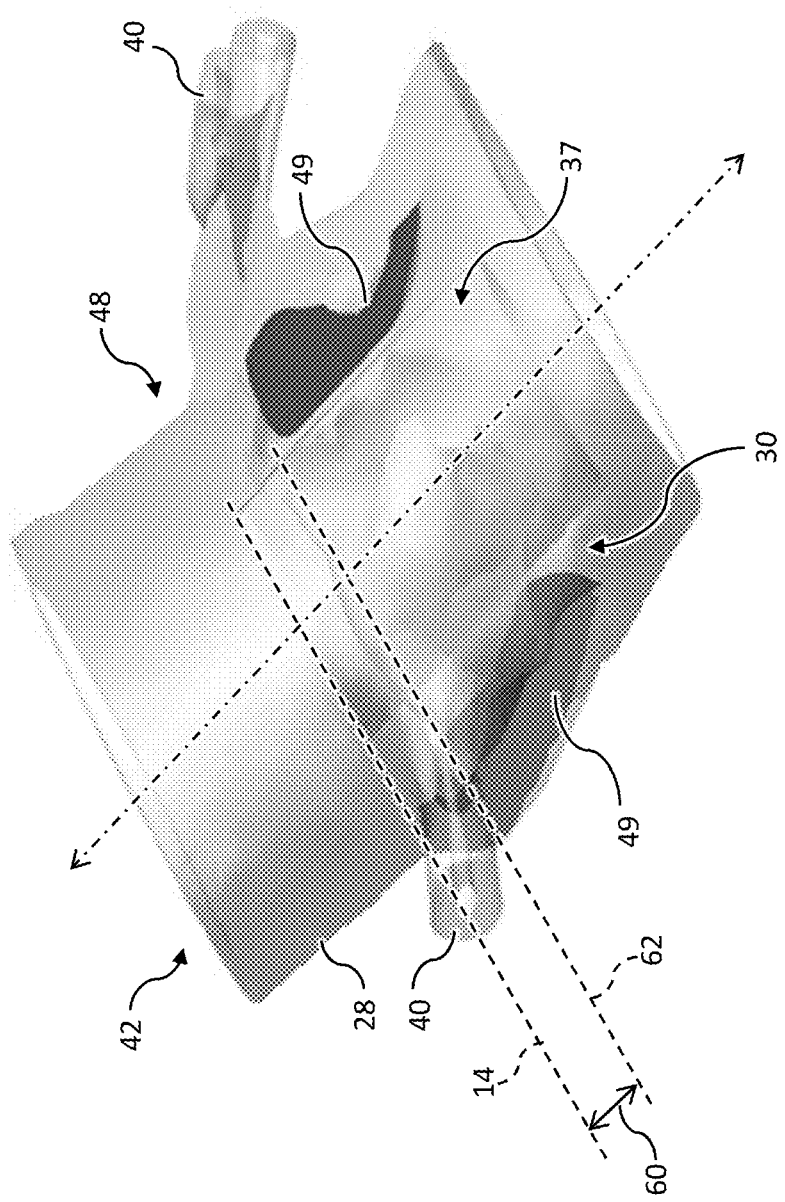
Figure 14:
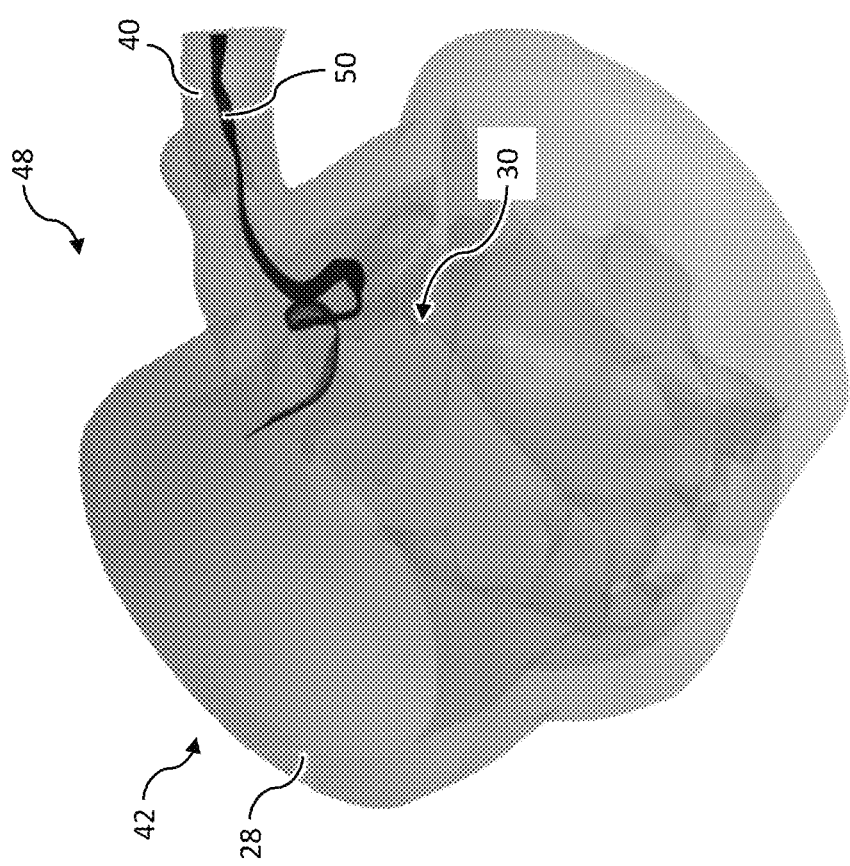

The numerical analysis engine 214 can further be programmed to simulate blood flow 49 properties for any of the deformed analytical models 42, such as shown in FIGS. 13 and 14. For example, the geometry of the deformed analytical model 42 corresponding to full deployment 48 of the surgical object 36 can be used for CFD to model blood flow 49 properties in aortic root 28 region under different conditions. In some examples, the blood flow 49 can be used to quantify paravalvular leakage. For example, the amount and rate of blood flow 49 flowing between the TAV 37 and the aortic root 28 can be indicative of the relative risk for paravalvular leakage. Alternatively or additionally, the blood flow 49 properties of the deformed analytical model 42 can quantify thrombosis. Thrombosis can correspond to localized coagulation or clogging of the blood induced by the TAVR.

The blood flow 49 can be used to identify the TAVR induced blood flow stasis zones. For example, the results of the blood flow 49 can be displayed on the display 208 to illustrate and quantify blood flow stasis zones. Accordingly, the blood flow stasis zones can be indicative of risk for thrombosis. Additionally, the CFD can be used to model a flow pattern 50 of contrast agent flow in coronary artery 40, which can be used to validate the numerical analysis engine 214 or the efficacy of the modeled clinical procedure with data collected during and/or following the clinical procedure. For example, comparing the arrangement of the calcific nodule 32 arrangement and flow patterns in the CFD relative to aortographic images captured during and/or after the clinical procedure can provide insight into the accuracy of deformed analytical model 42 and the CFD.

Referring collectively to FIGS. 1, 3, 4, 15, 16, 17, 18, 19, 20, and 21, the examples provided herein can further include a method 130 for predictive heart valve simulation. The method 130 can include a process 132 for generating parameters indicative of the anatomical regions 26 of the patient 20. In some examples, the parameters can be generated directly or indirectly based on the image data 22. For example, the image data 22 can include a plurality of slices of CT data 52 representative of the left coronary leaflet 54 and the right coronary leaflet 56, such as shown in FIGS. 16, 17, 18, and 19. The CT data 52 can be directly measured for determining parameters for the anatomical regions 26. The parameters can include, for example, a coronary ostium height relative to the annulus baseline, an annulus diameter, and/or a sinotubular junction (STJ) diameter, which can correspond to the final position of the coronary leaflets 30 after deployment.

Alternatively or additionally, model parameters can be determined based on the plurality of slices of CT data 52 of the left coronary leaflet 54 and the right coronary leaflet 56. The model parameters 58 can include a height h of coronary artery 40 from the annulus, a thickness t of the calcific nodule 32 on the left coronary leaflet 54, a thickness t of the calcific nodule 32 on the right coronary leaflet 58, a projection of coronary ostium diameter d on the annulus to STJ line, a sinus width w between coronary ostium and the annulus to STJ, a leaflet length l of the left coronary leaflet 54, and a leaflet length l of the right coronary leaflet 56. Since the aortic leaflets 30 undergo the most strain during diastole, the image data 22 can be captured in a diastolic phase of a cardiac cycle. In further examples, the parameters, the model parameters, or both can be generated based on the anatomical model data 24.

Figure 21:
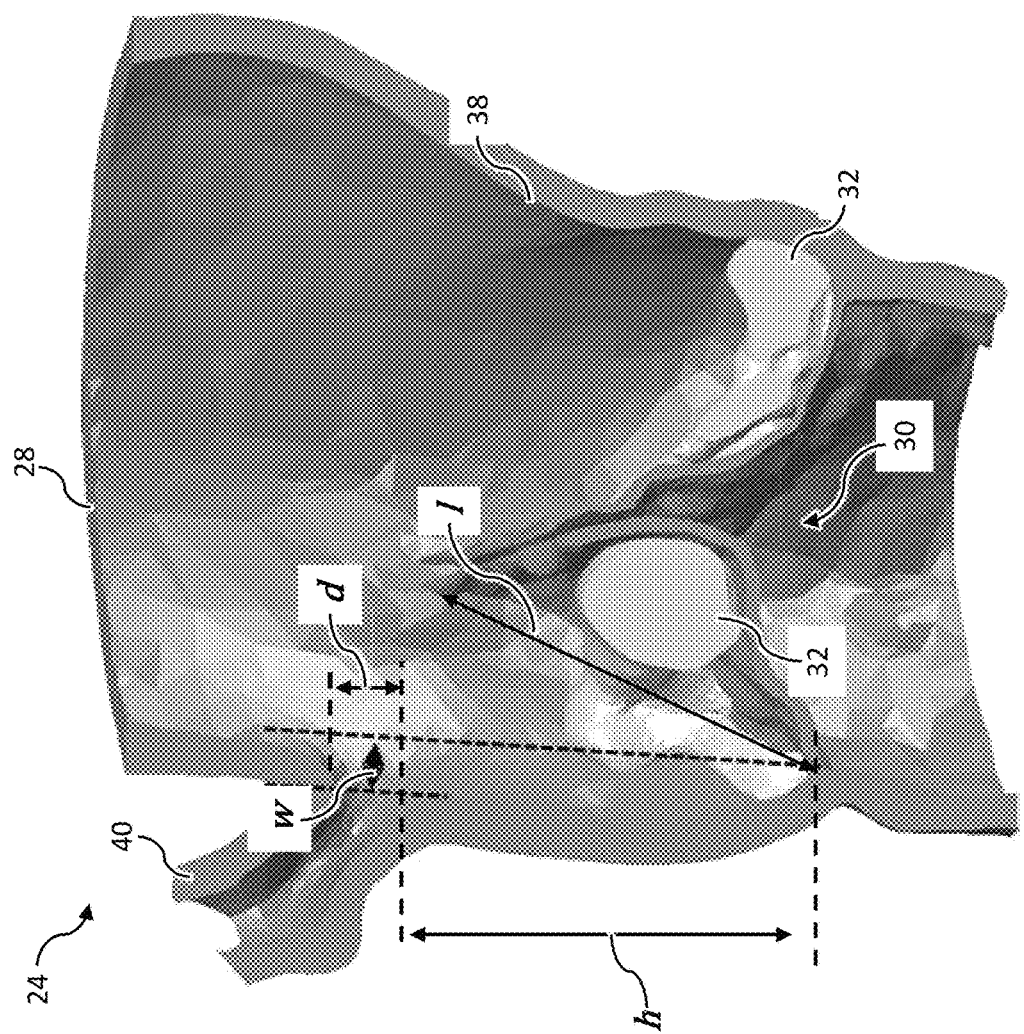
Figure 22:
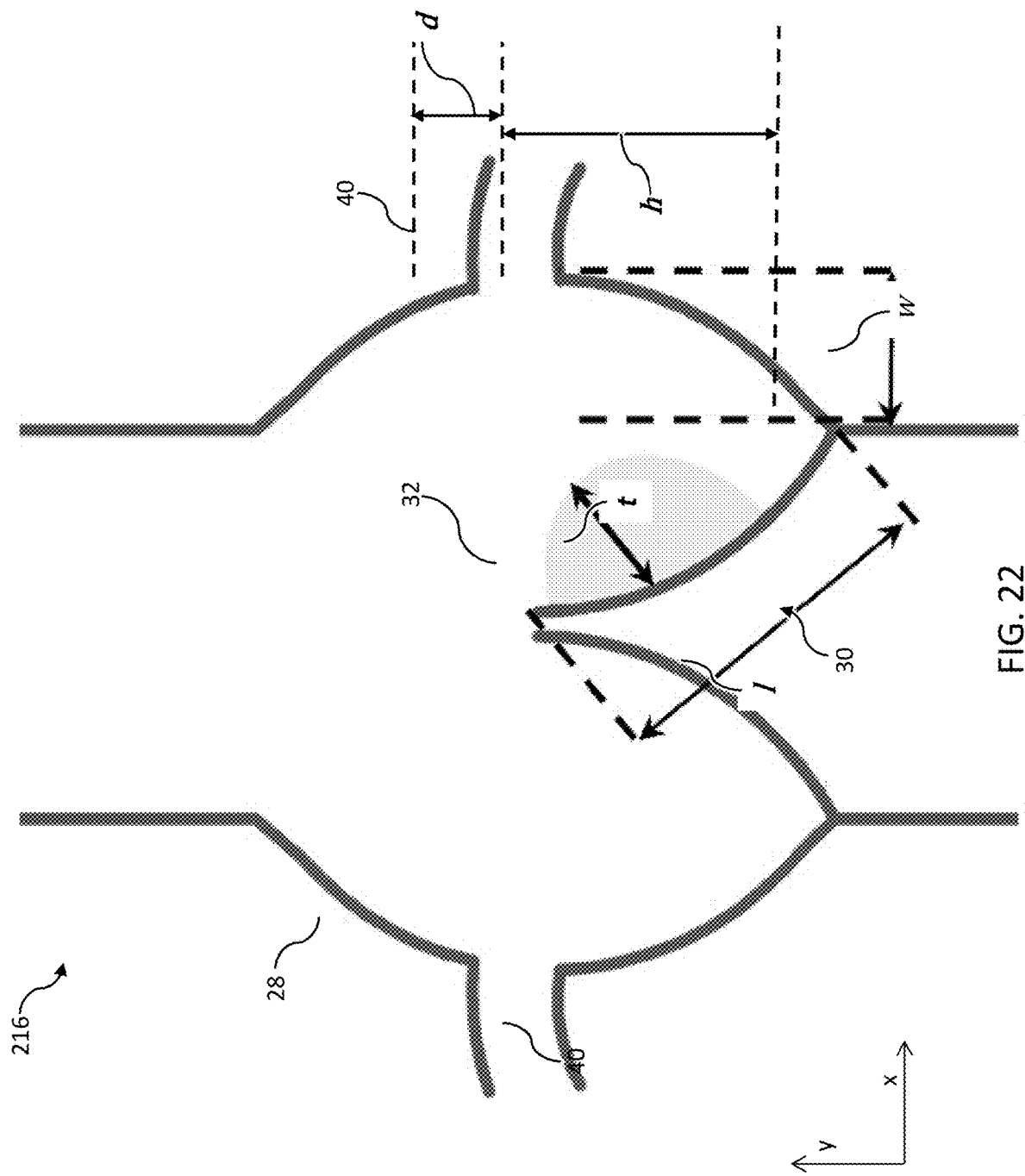
FIGS. 22-23 illustrate an example of a parametric analysis engine.
Figure 23:
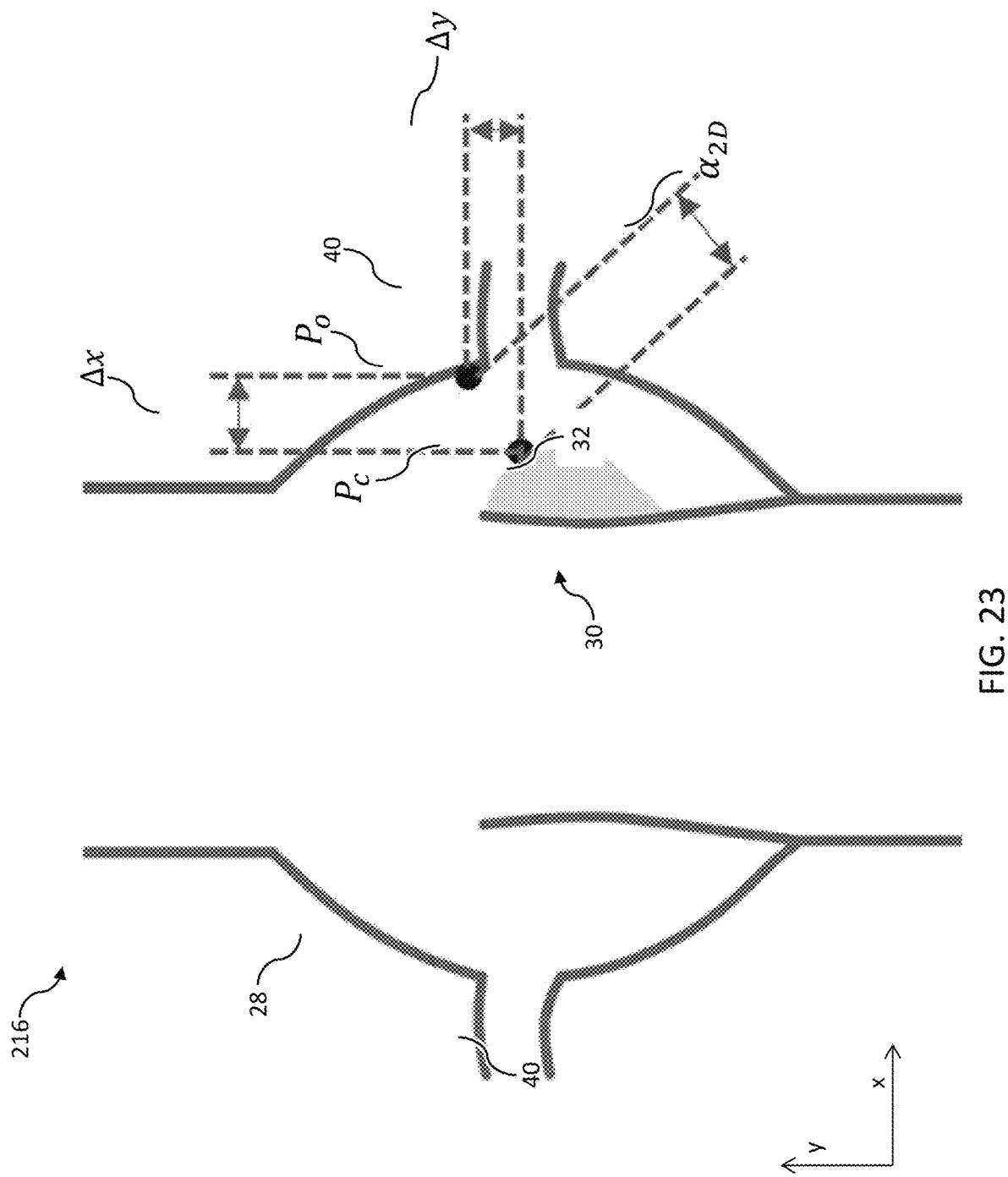

Referring collectively to FIGS. 1, 15, 22, and 23, the method 130 can further include a process 134 for simulating the clinical procedure. In some examples, the image analysis device 200 can be configured to execute a parametric analysis engine 216 provided on the memory 204. The parametric analysis engine 216 can be programmed to simulate the impact of the clinical procedure upon the size and the location of the calcium nodule 32 based on the model parameters. When the parametric analysis engine 216 simulates the TAVR, a gap size $\alpha_{2D}$ can be determined by modeling the coronary leaflets 30 in a fully expanded position (e.g., such as shown in FIG. 21) due to TAV stent deployment. The gap size $\alpha_{2D}$ can correspond to a two-dimensional distance between the tip of the coronary leaflet 30 and coronary ostium of the coronary artery 40. Generally, the gap size $\alpha_{2D}$ can be correlated to risk of coronary obstruction. It is noted that the parametric analysis engine 216 can be programmed to model anatomy of the patient 20 in two-dimensions to determine the gap size $\alpha_{2D}$.

The parametric analysis engine 216 can be further programmed to determine a location of two points: nodule point $P_C$, which can correspond to the position of the calcific nodule 32 of the aortic leaflet 30; and ostium point $P_O$, which can correspond to the position of the upper edge of the coronary ostium of the coronary artery 40. Accordingly, the gap size $\alpha_{2D}$ can be calculated by the parametric analysis engine 216 based on:

$$\alpha_{2D} = \sqrt{(\Delta x)^2 + (\Delta y)^2} \quad \text{(Equation 1)},$$

wherein $\Delta x$ is a horizontal offset (x-direction) between the nodule point $P_C$ and the ostium point $P_O$, and $\Delta y$ is a vertical offset (y-direction) between the nodule point between $P_C$ and the ostium point $P_O$.

The horizontal offset $\Delta x$ can be determined based on Equation 2 and the vertical offset $\Delta y$ can be determined based on Equation 3:

$$\Delta x = w - t \quad \text{(Equation 2)},$$

$$\Delta y = h + d - l \quad \text{(Equation 3)},$$

wherein the following model parameters can be used: the sinus width w at the ostium level of the coronary artery 40, the thickness t of the calcific nodule 32 on the tip of the aortic leaflet 30, the leaflet length l, height h of the coronary ostium of the coronary artery 40, and coronary ostium diameter d of the coronary artery 40.

The parametric analysis engine 216 can be further programmed to calculate the gap size $\alpha_{2D}$ for both left and right coronary ostium of the coronary arteries 40.

Figure 25A:
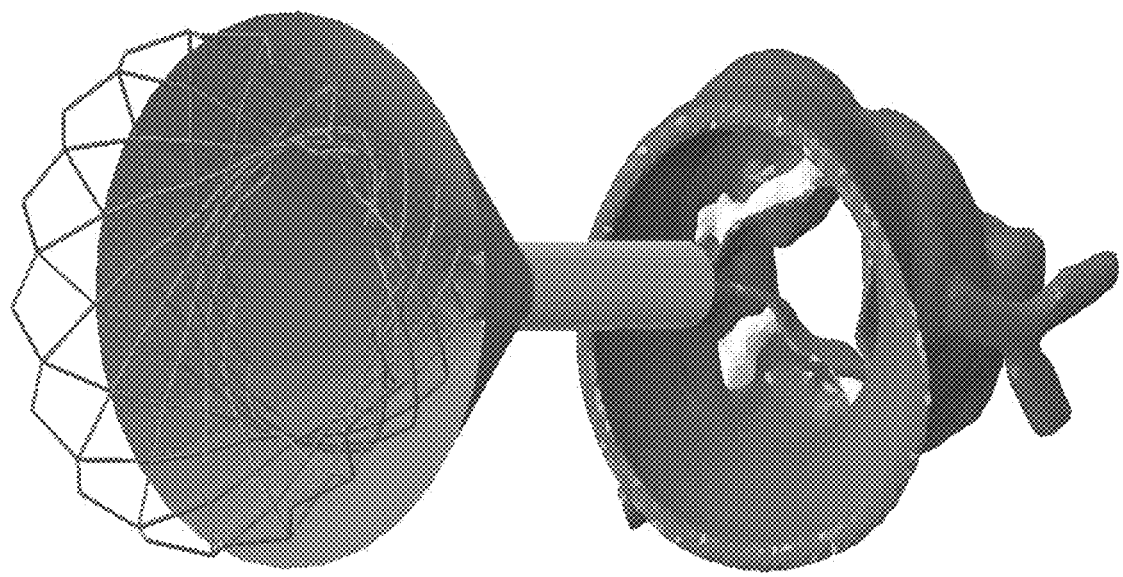
FIGS. 25A and 25B illustrate exemplary portions of a method for delivery of a self-expandable stent to a patient.
Figure 26:
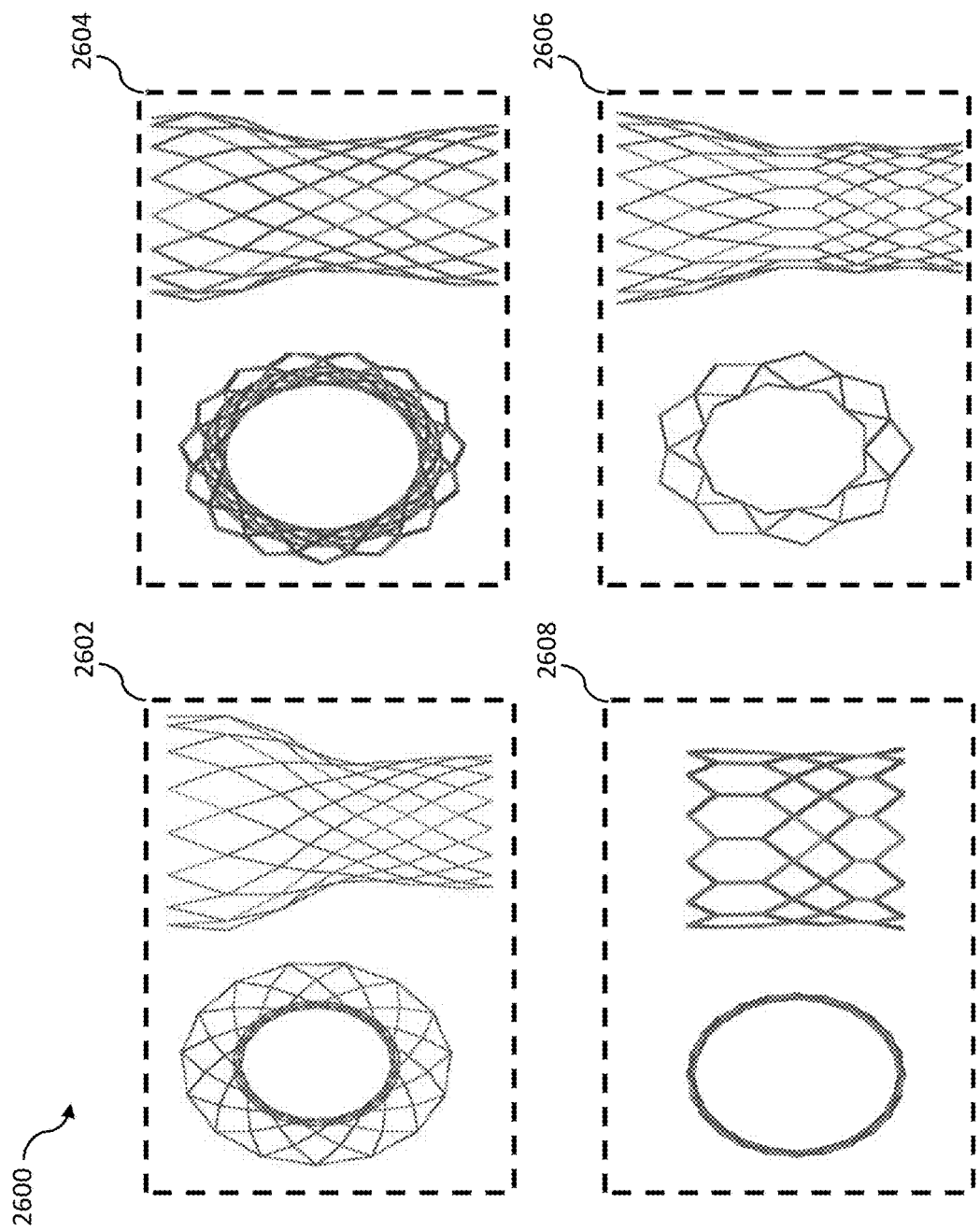
FIG. 26 illustrates exemplary self-expandable stents.

FIG. 24 illustrates an example of a method 2400 for delivery of a self-expandable stent to a patient. The self-expandable stent (or "stent") can correspond to any stent described herein, available, or can become available. In an example, the stent can correspond to a stent, such as shown in FIG. 26. The method 2400 can begin at step 2402, wherein models of patient-specific geometry can be generated and aligned with one or more objects. FIG. 25A illustrates a more detailed view of the step 2402, as shown in FIG. 24. In some examples, the models can include CAD models. The patient specific geometry can include an aortic wall, leaflets, and calcium nodules. The patient specific geometry can be aligned with a catheter (e.g., a cylinder with a given diameter based on a type of stent, e.g., valve type). The patient specific geometry can further be aligned with a crimper (e.g., a funnel with a diameter substantially equal to the diameter of the catheter, and with a greater diameter than an in-flow diameter of the stent). The patient specific geometry can further be aligned with the self-expandable stent (e.g., a TAV stent).

At 2404, a crimper can be employed to gradually crimp the stent. At 2406, the crimper simultaneously with the catheter can be configured to move toward the self-expandable stent (e.g., displacement boundary condition in an axial direction) such that bottom nodes of the TAV stent and the catheter are in a similar plane. The bottom nodes of the TAV stent can be fixed in a radial direction and free in other directions (e.g., axial and circumferential direction).

Figure 25B:
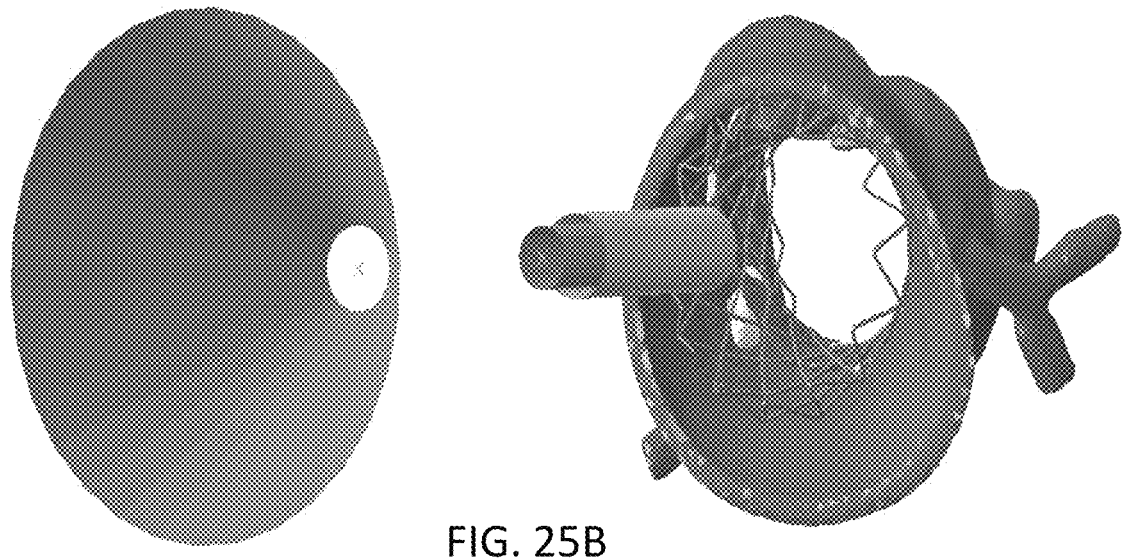

At 2408, the catheter along with the crimped TAV stent can be implanted at an aortic site (e.g., an aortic root) while the crimped TAV stent can be located inside the catheter. A particular location of a valve differs in patients, and can depend on anatomical factors of the patient specific geometry At 2410, while bottom nodes of the TAV stent are fixed in the radial direction and free in the other directions (e.g., axial and circumferential directions), the catheter can be configured to release the TAV stent gradually (e.g., the displacement boundary condition in the axial direction). At 2412, the catheter can be removed, and the TAV stent can be in the fully expanded configuration at the aortic site. FIG. 25B illustrates a more detailed view of the step 2412, as shown in FIG. 24.

After deployment the TAV stent outcomes of the clinical procedure can be evaluated. A final position of the native leaflets and calcium nodules relative to coronary arteries can be presented based on proper slices. The final configuration of the TAV can be analyzed. All the stress distributions on either the patient-specific geometry or TAV can be measured for further evaluations according to the systems and methods described herein. The material that can be used for the TAV stent can include Nitinol. The material properties of the patient-specific geometry can be modeled according to a hyper-elastic model. Calcium nodules can be modeled according to a linear-elastic model. Both crimper and catheter can be modeled as a rigid models.

In an example of an aortic valve replacement, the TAV stent can be positioned relative to the aortic site such that risks associated with a TAVR procedure can be substantially mitigated based on the systems and methods described herein. Such risks can include, but not limited to, coronary obstruction, paravalvular leakage, and thrombosis. Based on the systems and methods described herein, the stent can be positioned relative to the aortic site such that the stent can be deployed at the aortic site with zero to minimal resulting complications. Thus, the systems and methods described herein can substantially improve an accuracy and quality of a TAVR procedure, and thereby substantially reduces the risks associated with the procedure. Accordingly, the systems and methods described herein can be used a framework to quantify a risk (e.g., coronary obstruction) associated with the TAVR procedure prior to the procedure.

The quantified risk can be used to control the subsequent TAVR procedure. The systems and methods described herein can be used to predict risks associated with the TAVR procedure, and can be used to control the TAVR procedure such that the risks associated with the procedure are substantially mitigated. Controlling the TAVR procedure can include controlling one or more parameters of the TAVR procedure. The one or more parameters can include an orientation of the stent relative to the aortic site, a valve type and size, prior coronary protection, paravalvular leak consideration, and a need for the TAVR procedure.

FIG. 26 illustrates exemplary stents 2600 according to the systems and methods described herein. The exemplary stents 2600 can include a plurality of stents that can have varying diameters. Alternatively, the exemplary stents can include a plurality of stents that can have substantially similar diameters. The exemplary stents 2600 can include a plurality of self-expandable stents 2602, 2604, and 2606, and a balloon expandable stent 2608.

Figure 27:
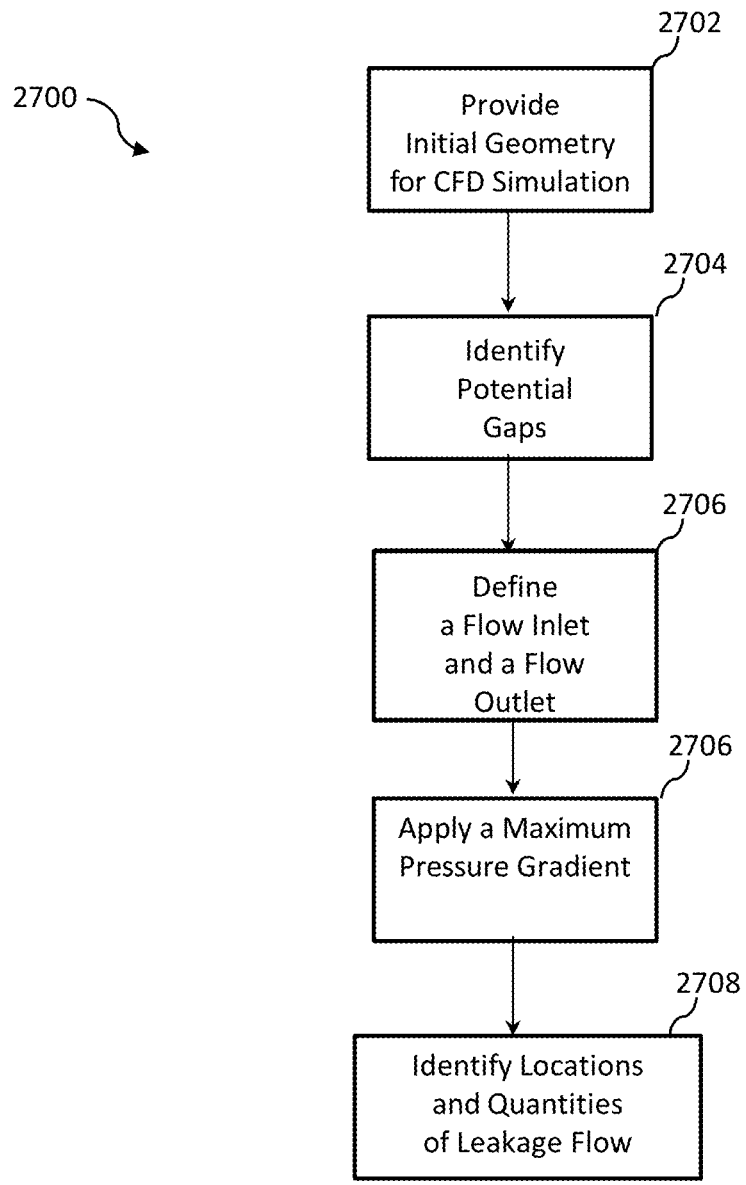
FIG. 27 illustrates an exemplary method for predicting and quantifying paravalvular leakage.

FIG. 27 illustrates an exemplary method 2700 for predicting and quantifying paravalvular leakage. The method 2400 can begin at step 2702, wherein after deployment of a TAV stent inside a patient-specific geometry, a final configuration of the TAV stent and the patient-specific geometry can be used as an initial geometry for CFD simulations. At 2704, potential gaps between the TAV stent and an inner wall of the patient-specific geometry can be identified for paravalvular leakage by applying a simulated blood flow from the ascending aorta relative to a left ventricle of the heart. At 2706, a section at an ascending aorta (e.g., top surface) can be defined as a flow inlet, and a section at the left ventricle can be defined as a flow outlet. At 2708, a maximum pressure gradient between the left ventricle and ascending aorta can be applied at the inlet. The outlet pressure can be set to zero such that the gradient can cause the fluid to flow from the inlet to the outlet. Since leakage flow is being studied, the flow can be in a reverse direction compared to a flow exiting the aortic valve. At 2710, after obtaining the steady state solution, locations and quantities of leakage flows can be measured based on jet velocity.

EXAMPLES

The examples provided herein were evaluated based on CT images of nine (9) patients who underwent TAVR. Three of the patients experienced coronary obstruction. Each of the patients were evaluated based on CT images acquired prior to TAVR. Using a parametric analysis engine (e.g., the parametric analysis engine 216, such as shown in FIG. 1), the gap size $\alpha_{2D}$ was calculated for both the left and right coronary arteries of the nine patients. The values as well as clinical statuses of the nine patients studied are summarized below in Table 1.

TABLE 1

| | Measurements from Patients | | | | | | |
|---|---|---|---|---|---|---|---|
| Patients # | $\alpha_{2D}$ for Left Coronary Ostium (mm) | $\alpha_{2D}$ for Right Coronary Ostium (mm) | $\alpha_{3D}$ for Left Coronary Ostium (mm) | $\alpha_{3D}$ for Right Coronary Ostium (mm) | Coronary Obstruction Risk Level | TAVR Operation Completed | Coronary Obstruction Confirmation |
| A | 14.78 | 7.52 | 12.38 | 7.4 | low | Yes | No |
| B | 3.53 | 3.62 | 2.58 | 3.39 | low | Yes | No |
| C | 8.69 | 5.96 | 6.68 | 7.07 | low | Yes | No |
| D | 3.87 | 2.26 | 4.6 | 2.54 | moderate | Yes | No |
| E | 0.98 | 5.69 | 0.93 | 6.4 | high | No | n/a |
| F | 2.16 | 2.24 | 0.85 | 3.13 | high | No | n/a |
| G | 0.60 | 4.24 | 0.7 | 7.46 | high | Yes | Yes |
| H | 7.50 | 6.85 | 5.99 | 6.33 | low | Yes | Yes |
| I | 0 | 0 | 0 | 0 | high | Yes | Yes |

After evaluating the gap size $\alpha_{2D}$ values for the nine patients, the nine patients were categorized into three groups: low risk, moderate risk, and high risk of coronary obstruction for either coronary ostia. Four of the patients were categorized as low risk, one patient was categorized as moderate risk, and four of the patients were categorized as high risk. The TAVR status and the occurrence of coronary obstruction is also shown in Table 1. Of the four patients who were placed in the high risk category, two patients underwent TAVR (Patient G and Patient I). Patient G and Patient I were confirmed to experience coronary obstruction. For Patient G, the coronary obstruction proved fatal. Patient I was successfully rescued via open heart intervention.

Patient H was characterized as low risk. While patient H did experience coronary obstruction, the coronary obstruction was due to blockage from prosthetic leaflet subannular membrane material, and not blockage from the native leaflets. Patient H was successfully rescued via open heart intervention. For the other two high risk patients, Patient E declined any surgical intervention because of the high risk, and Patient F was admitted for open heart surgery. The remaining moderate and low risk patients successfully underwent TAVR without coronary obstruction.

Figure 28:
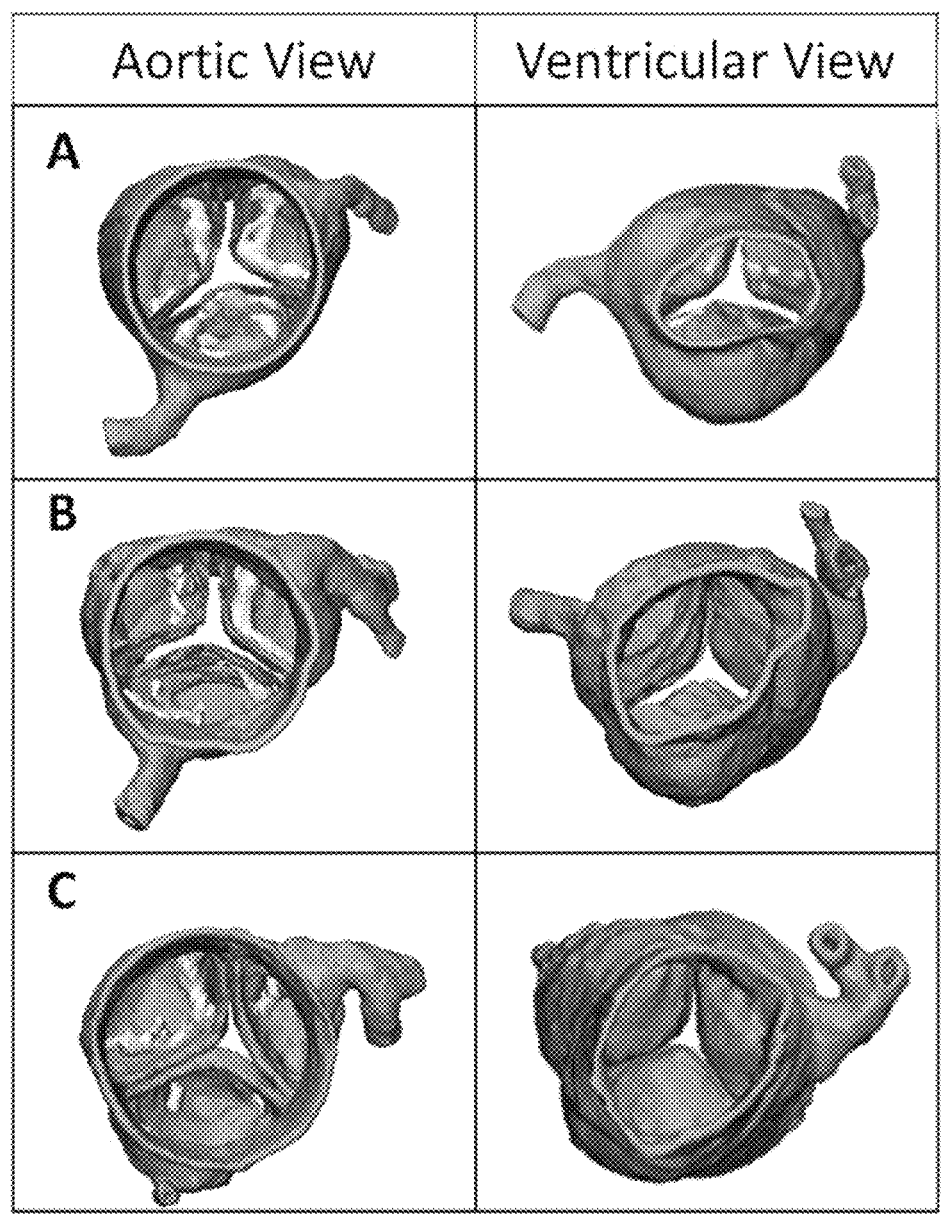
FIGS. 28-30 illustrate exemplary anatomical model data collected during a patient study.
Figure 29:
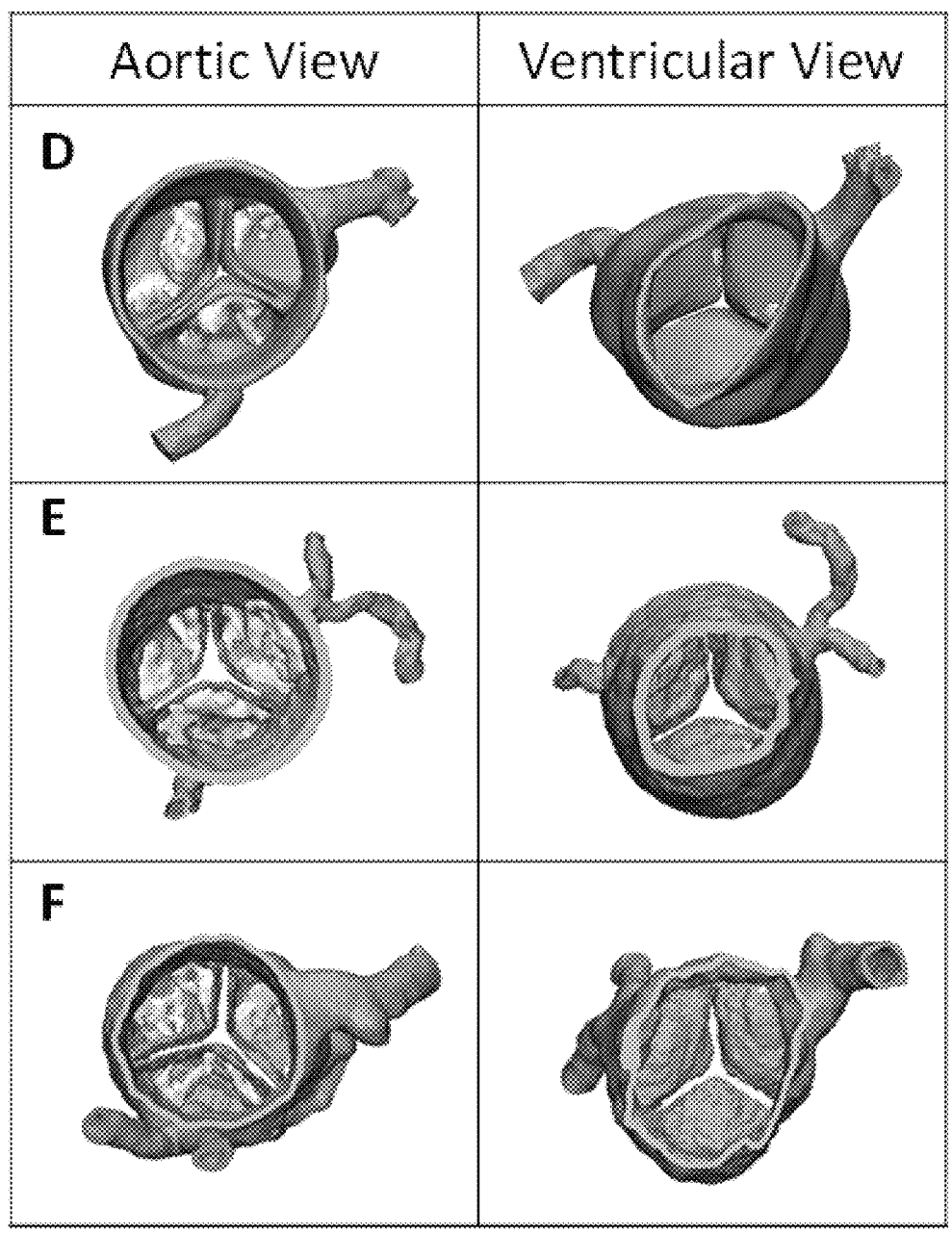
Figure 30:
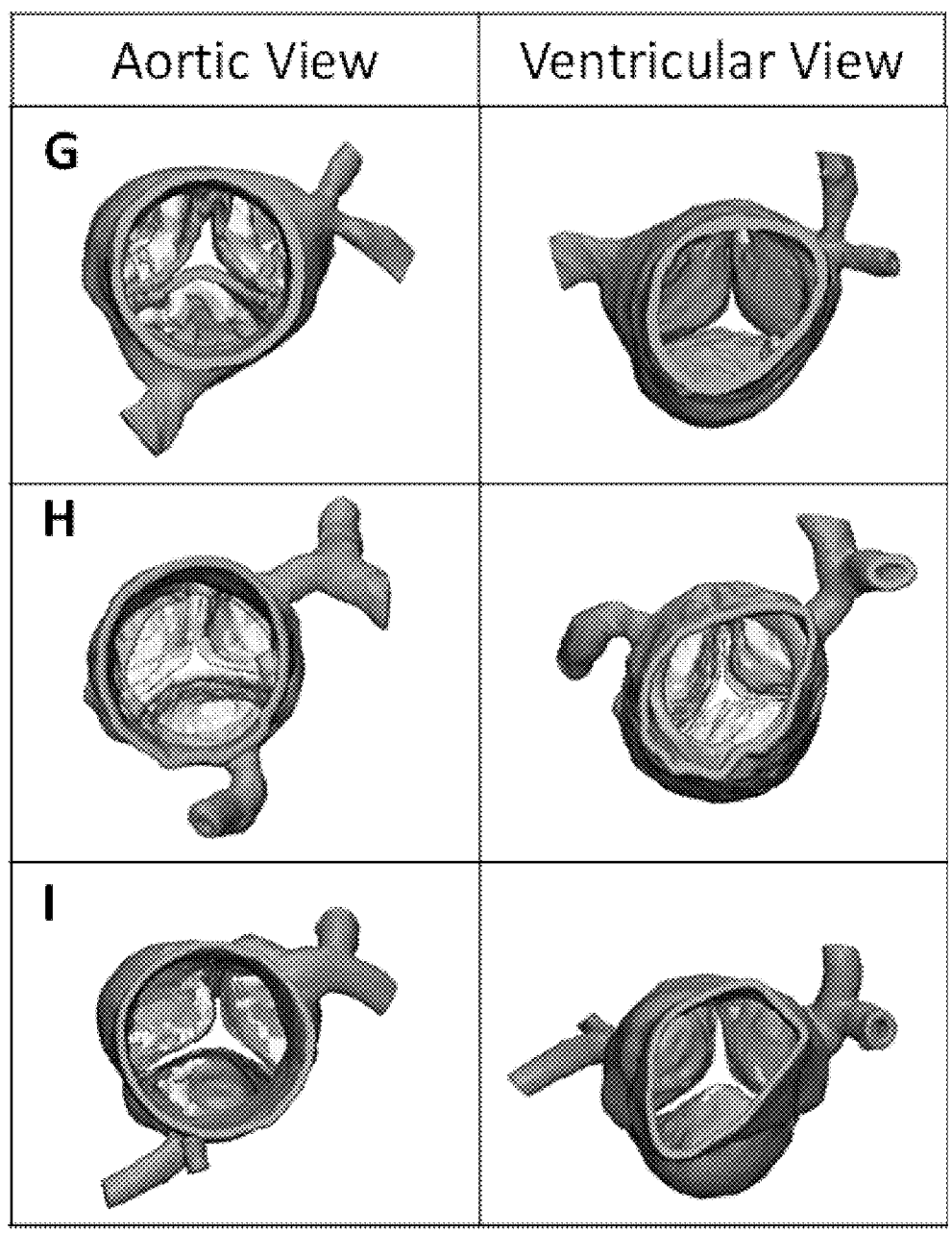

Referring collectively to FIGS. 28, 29, and 30, anatomical model data was reconstructed for each of the patients. Aortic and ventricular views of the anatomical model data for each patient's reconstructed aortic root geometry are provided. Aortic views are oriented with the commissure of non and left coronary cusps on top. In the ventricular views, however, the top commissure corresponds to the left and right coronary cusps. Calcific nodules (colored yellow) were reconstructed separately from the aortic root (colored red) and then added to the leaflets. The geometry for Patient H, who has a failed bioprosthetic surgical valve implanted is colored in grey. Although basic characteristics of all the patients such as tri-leaflet valves, two coronary arteries, and arrangement of the cusps are similar, each patient has a unique aortic geometry with different patterns and severity of calcification (e.g., different size, shape, and position of calcific nodules).

Figure 31:
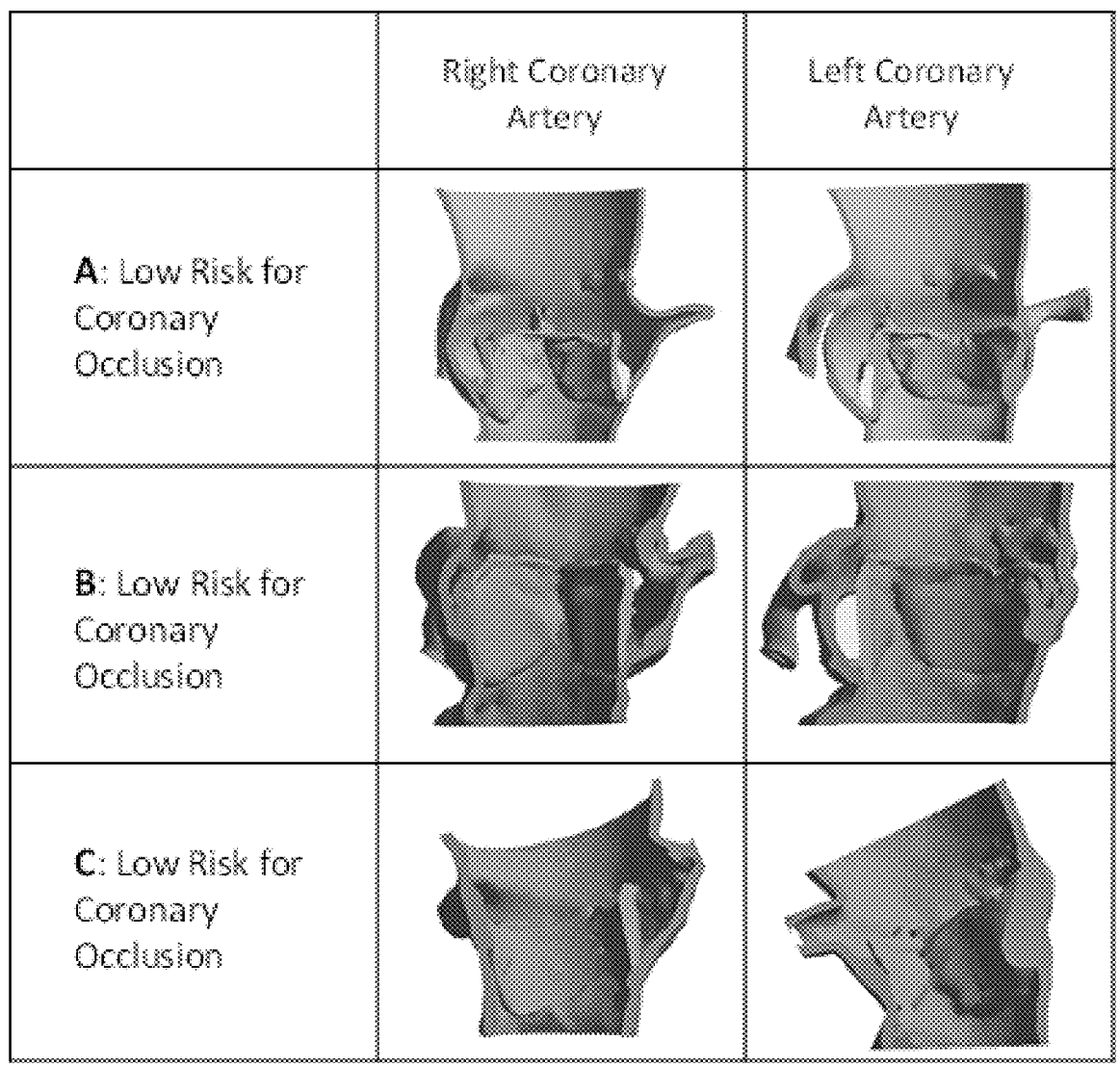
Figures 34, 35:
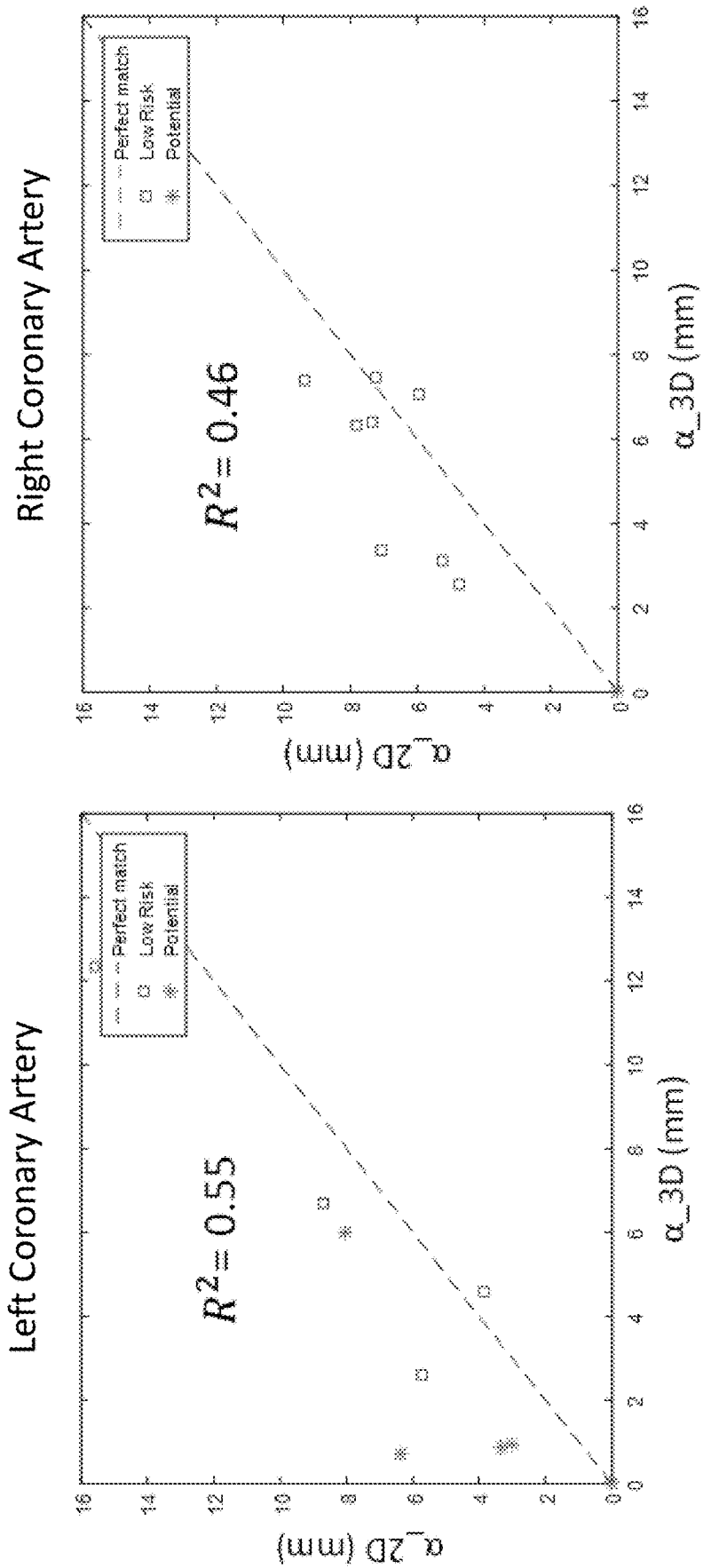
FIGS. 34-39 illustrate exemplary ordered pairs of gap sizes collected during the patient study.
Figures 36, 37:
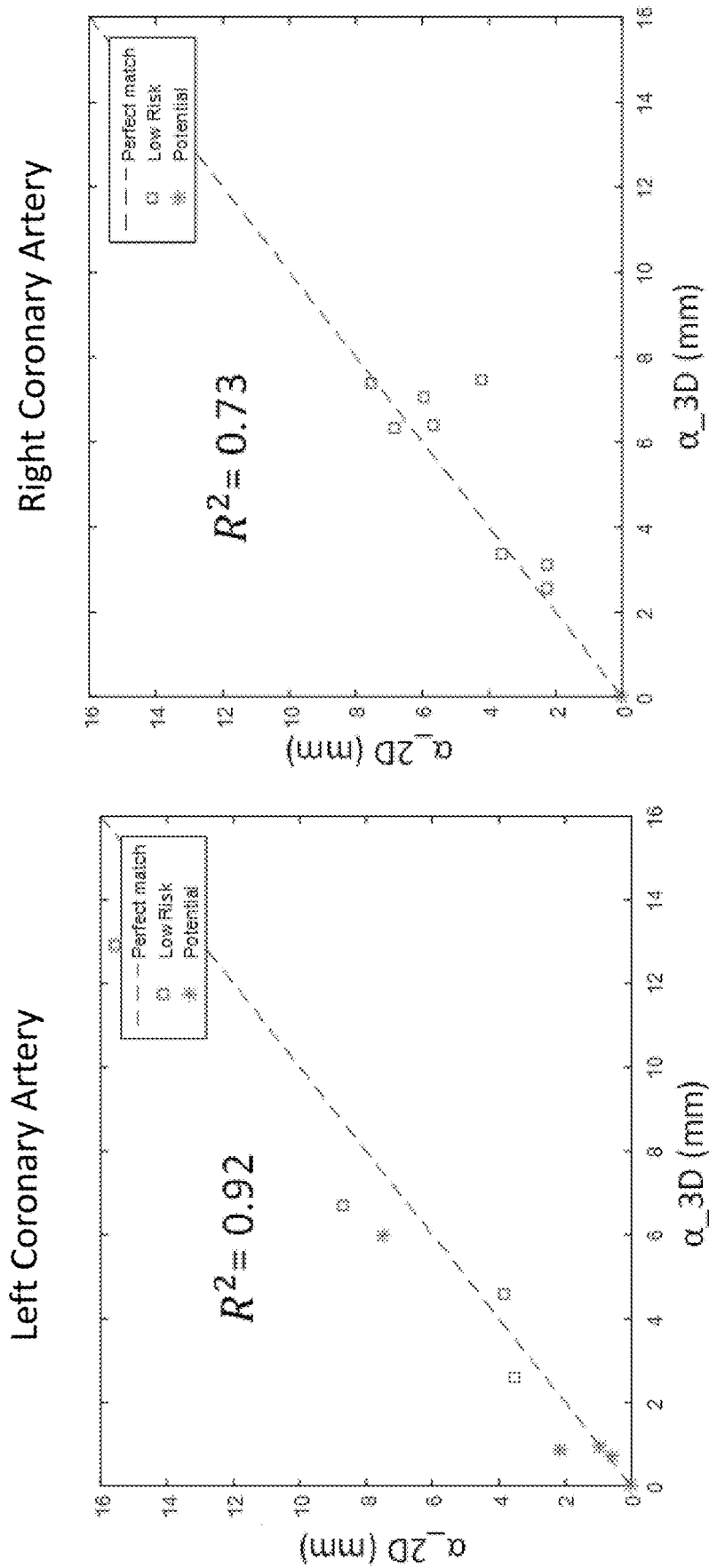

Referring collectively to FIGS. 31, 32, and 33, analytical model data was generated based on the anatomical model data. The numerical analysis engine was used to determine deformed analytical models based on the analytical model data. The deformed analytical models corresponding to TAV stent deployment were extracted. Cross-sectional views of both left and right coronary arteries were selected from the three-dimensional geometry to show the final position of leaflets relative to the left and right coronary ostia. These cross-sections include the ostium centerline as well as maximum calcification thickness on the leaflet tip. Cross-sectional views of simulated post-deployment anatomy of the nine patients for both left and right coronary ostium are provided. For ease of recognition, the edge of the leaflets are highlighted in red, and calcific nodules on the leaflets are highlighted in yellow. For patients previously determined the parametric analysis engine as being high risk for coronary obstruction, the three-dimensional cross-sectional views also illustrate the possibility of the native leaflets blocking the ostia.

The gap size $\alpha_{3D}$ for each of left and right coronary ostia was measured based on the deformed analytical models. The gap size $\alpha_{3D}$ for each of the patient is summarized above in Table 1. Based on the gap size $\alpha_{3D}$, the patients were again categorized as low risk, moderate risk, or high risk for coronary obstruction. The categorization based upon the gap size $\alpha_{3D}$ agreed well with the categorization based upon the gap size $\alpha_{2D}$. Patients A, B, C, and H were categorized as low risk for coronary ostia obstruction due to stent deployment, Patient D was categorized with potential obstruction of the right coronary ostia, and Patients E, F, G, and I were categorized as having high risk of left coronary ostium obstruction.

Figure 38:
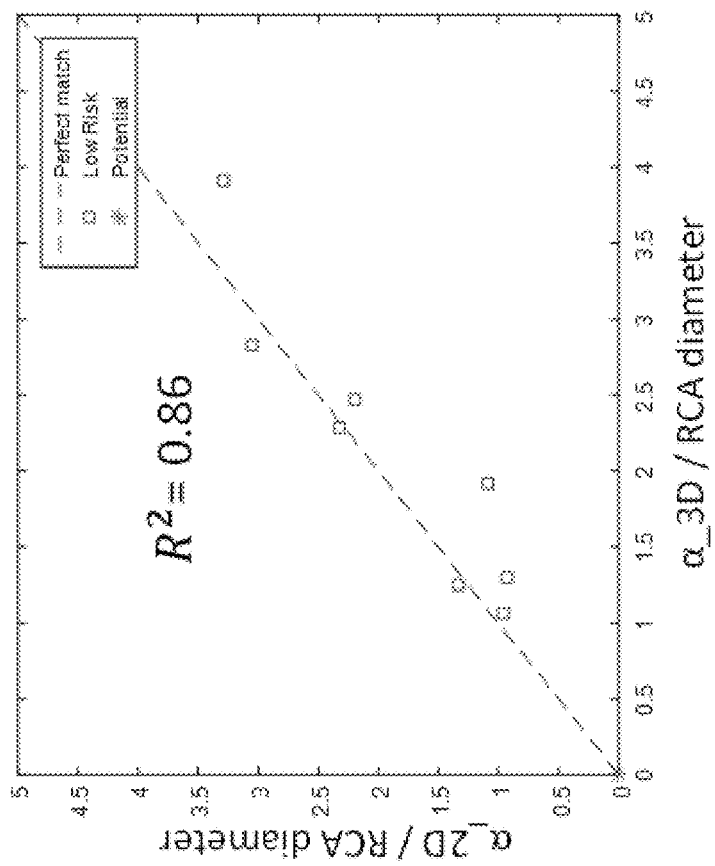
Figure 39:
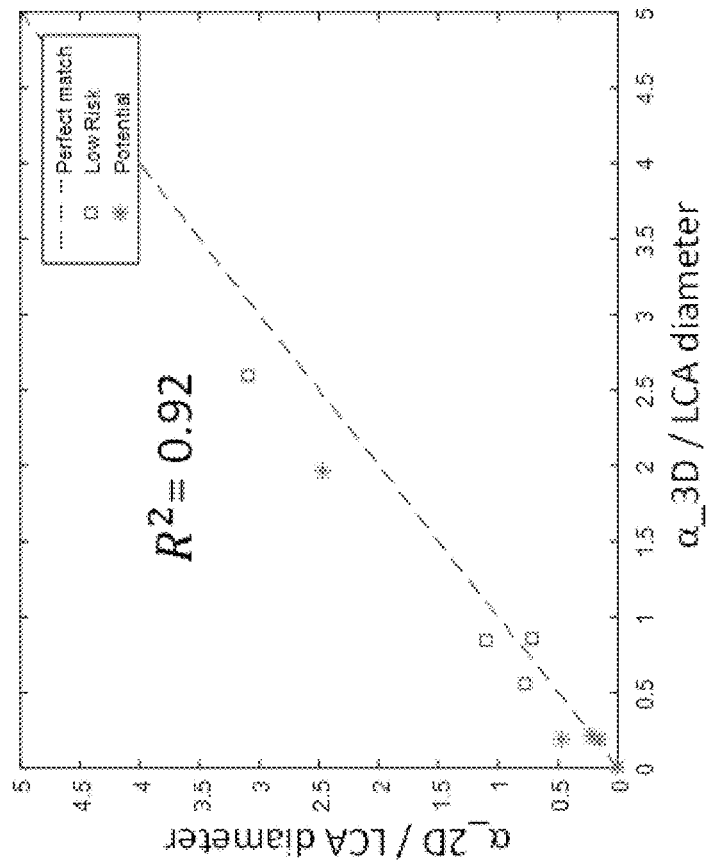

Referring collectively to FIGS. 34, 35, 36, 37, 38, and 39, after determining gap size $\alpha_{2D}$ based on model parameters obtained from CT images, and gap size $\alpha_{3D}$ using the numerical analysis engine, gap size $\alpha_{2D}$ data were plotted against gap size $\alpha_{3D}$ data for both left and right coronary arteries of each patient. The $\alpha_{2D}=\alpha_{3D}$ regression line is depicted in FIGS. 34, 35, 36, 37, 38, and 39 to provide reference for perfectly matched data. The $R^2$ value, which is a statistical parameter indicating closeness of data points to the fitted regression line, is also depicted. Red data points indicate patients with high-risk coronary obstruction, and blue points show patients with low-risk coronary obstruction. The results depicted in FIGS. 34 and 35 were determined by neglecting calcification thicknesses for the calculation of gap size $\alpha_{2D}$. The $R^2$ value for the left coronary artery was 0.55 and the $R^2$ value for the right coronary artery was 0.46. The gap size $\alpha_{2D}$ data depicted in FIGS. 36 and 37 were determined considering the leaflet tip calcific nodule thickness. The $R^2$ value for the left coronary artery was 0.92 and the $R^2$ value for the right coronary artery was 0.73. Thus, after including the calcific nodule size effect, a significant improvement was observed in the $R^2$ values. Any of the gap sizes provided herein can include a normalized gap size that is normalized according to an anatomical distance. For example, the gap size $\alpha_{2D}$ data and gap size $\alpha_{3D}$ data depicted in FIGS. 36 and 37 were normalized according to the respective diameter of the left coronary artery and right coronary artery. The normalized data is depicted in FIGS. 38 and 39. The normalized data showed further improvement of the $R^2$ values. The $R^2$ value for the left coronary artery was 0.92 and the $R^2$ value for the right coronary artery was 0.86. Likewise the gap size for paravalvular leakage can be normalized for by an anatomical distance of the patient.

According the examples described herein, calcification thickness on the leaflet tip can be used to construct a normalized cut-off factor to evaluate risk of coronary obstruction prior to TAVR. As noted above, neglecting calcium nodule thickness in the calculation of the gap size $\alpha_{2D}$, e.g., based only on coronary height, leaflet length, and sinus width at the coronary ostium, can lead to overestimation of the gap size $\alpha_{2D}$ for patients with high risk, under predicting the level of risk for coronary obstruction. Additionally, the comparison of the gap size $\alpha_{3D}$ and the gap size $\alpha_{2D}$ showed relatively weak correlations (e.g., $R^2$ value for the left coronary artery was 0.55 and the $R^2$ value for the right coronary artery was 0.46). Considering calcific nodule thickness in the calculation of the gap size $\alpha_{2D}$ can improve the correlation with the gap size $\alpha_{3D}$, e.g., the $R^2$ value for the left coronary artery was 0.92 and the $R^2$ value for the right coronary artery was 0.73.

To further improve the correlation, normalized equivalent parameters were determined for both the gap size $\alpha_{2D}$ and the gap size $\alpha_{3D}$ by normalizing the gap size $\alpha_{2D}$ and the gap size $\alpha_{3D}$ with respect to their corresponding coronary artery diameter. Consequently, normalization led to a clear cut-off ratio of 0.50 for patients with confirmed or high risk coronary obstruction. This ratio provides an indication that coronary obstruction is likely probable when the final distance between the native leaflets and ostium, e.g., the gap size $\alpha_{2D}$ or the gap size $\alpha_{3D}$, is less than about half of the corresponding coronary artery diameter.

It should now be understood that the examples described herein relate to systems and methods for quantifying a prediction of coronary obstruction in patients with severe aortic stenosis prior to TAVR. For example, model parameters including the position and location of calcific nodules can be collected and provided to a parametric analysis engine to predict an amount of coronary blockage that can result from the TAVR. Alternatively or additionally, analytical model data can be generated based on the three dimensional geometry of the patients anatomy. A numerical analysis engine can analyze the analytical model data to generate deformed analytical models. Accordingly, the amount of coronary blockage resulting from the TAVR can be quantified according to patient specific morphologies of the aortic root.

Moreover, the systems and methods described herein can be used to evaluate patient geometrical factors prior to TAV implantation based on CT image data. For example, various types and sizes of valves can be evaluated in order to identify a valve and diameter size that is best suited for the patient. In addition to the valve itself, the evaluations can prevent complications such as coronary artery ostium obstruction. Despite the life-threatening nature of coronary artery ostium obstruction, existing valve manufacturers have no specific safety guidelines in place to minimize the chance of coronary ostium obstruction. Moreover, manufacturer guidelines are often neglected by surgeons who have successfully performed operations outside of the guidelines.

Further advantages of the systems and methods described herein include providing a more accurate cut-off factor that is more suited to prevent coronary ostium obstruction. For example, while some studies have identified contributing factors such as coronary height, SOV diameter, and leaflet lengths, the studies have failed to consider the effect of calcific nodule size and location. The systems and methods described herein can be used to quantify an impact of calcific nodules on the amount of coronary ostium obstruction (e.g., gap sizes or normalized gap sizes) expected to be experienced due to TAVR.

The systems and method described herein can make use of three-dimensional anatomical model data to improve an accuracy and consistency of collecting parameter information. For example, CT image data of an aortic root geometry can include a series of slices, each of which can represent specific cross-sections of the patient's anatomy. The accuracy of a measured parameter can be a function of the slice selected for measurement. Since slice selection is use-defined, technicians can introduce bias (e.g., errors) when measuring parameters. The three-dimensional anatomical model data can substantially mitigate technician bias. For example, cross-sections can be generated from any portion of the data, and not just the native image orientation. Accordingly, the most severe aspects of the patient's anatomy can be used to collect parameter measurements. Moreover, the deformed analytical models can provide a full representation of the impact of various stages of a clinical procedure.

Further improvements to TAVR can be provided by real time comparisons of various simulated parameters of the TAV including a type of TAV, a size of TAV, and positioning of the TAV. For example, prior to conducting TAVR, a clinician (e.g., a surgeon) can use the patients anatomical information to simulate various deformed models of the patients anatomy. Accordingly, the sensitivity of the patient to particular positioning of each available model of TAV can be evaluated. For example, each model of TAV can be provided in various positions and the relative amount of risk for complications such as, coronary obstruction, paravalvular leakage, and thrombosis, can be quantified. Moreover, the deformed models and quantified information can be displayed (e.g., in virtual reality) to allow the clinician to have visual feedback of the results of the TAVR prior to performing the TAVR. Accordingly, the clinical procedure can be performed with greater control, lower risk, and substantially improved patient outcomes.

It is noted that the terms "substantially" and "about" can be used herein to represent an inherent degree of uncertainty that can be attributed to any quantitative comparison, value, measurement, or other representation. These terms are also used herein to represent a degree by which a quantitative representation can vary from a stated reference without resulting in a change in the basic function of the subject matter at issue.

What have been described above are examples. It is, of course, not possible to describe every conceivable combination of components or methods, but one of ordinary skill in the art will recognize that many further combinations and permutations are possible. Accordingly, the disclosure is intended to embrace all such alterations, modifications, and variations that fall within the scope of this application, including the appended claims. Additionally, where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. A computer implemented method to predict complications prior to an implantation of a trans-catheter valve in the heart, the method comprising:
   executing, by at least a processor, program code stored in a non-transitory computer-readable-medium to perform a simulation, comprising:
   generating first anatomical model data based on image data characterizing anatomical regions of a heart of a patient, wherein the first anatomical model data comprises three-dimensional shapes of the anatomical regions of the heart comprising a left coronary leaflet, a right coronary leaflet, a non-coronary leaflet, an aortic root, left and right coronary ostia, an ascending aorta, and left and right coronary arteries;
   generating first analytical model data based on the first anatomical model data, wherein the first analytical model data comprises a three-dimensional (3-D) mesh of the anatomical regions of the heart including at least parametric measurements comprising: a height h of coronary artery from an annulus baseline, a sinus width w at an ostium level, a thickness $t_1$ of a calcific nodule formed on the left coronary leaflet, a thicknesses $t_2$ of a calcific nodule formed on the right coronary leaflet, and a leaflet length $l_1$ of the left coronary leaflet and a leaflet length $l_2$ of the right coronary leaflet, and a coronary diameter d;
   generating a first deformed analytical model based on the first analytical model data and based on a three-dimensional mesh of a virtually implanted trans-catheter valve, wherein the first deformed analytical model is indicative of a first deformed position of the anatomical regions of the heart and a first deformed position of the virtually implanted trans-catheter valve, wherein the generating of the first deformed analytical model comprising:
      calculating respective gap sizes $\alpha_{2D1}$, $\alpha_{2D2}$ in a fully expanded configuration of the virtually implanted trans-catheter valve, wherein the $\alpha_{2D1}$, $\alpha_{2D2}$ are calculated using a parametric model based on the virtually implanted trans-catheter valve, each of the $\alpha_{2D1}$, $\alpha_{2D2}$ corresponds to a minimum two-dimensional distance between two points separated by a point Pc and an ostium point Po, wherein the point Pc corresponds to a nearest point on the left coronary leaflet and on the right coronary leaflet relative to Po, and the ostium point Po corresponds to an upper edge of the corresponding coronary ostium, and
      calculating respective gap sizes $\alpha_{3D1}$, $\alpha_{3D2}$ in the fully expanded configuration the virtually implanted trans-catheter valve, wherein the $\alpha_{3D1}$, $\alpha_{2D2}$ each corresponds to a respective minimum three-dimensional distance between the ostium point Po and the left coronary leaflet and on the right coronary leaflet, respectively;
      establishing, from a database of image data from patients with and without coronary obstruction event after having implanted trans-catheter valves, a an optimal patient-specific predictive criteria of confirmed coronary obstruction, by performing systematic data-fitting on at least the respective gap sizes $\alpha_{2D1}$, $\alpha_{2D2}$, $\alpha_{3D1}$, $\alpha_{3D2}$ in combination with evaluating variables comprising one or more of: valve size and type, parametric measurements from the first deformed analytical model data and the first anatomical model data,
   wherein the first deformed analytical model data further correspond to the virtually implanted trans-catheter valve with full deployment configurations comprising different depths, yaw, and pitch angles relative to a center line of an aortic root, and
   wherein the performing of the systematic data-fitting comprising one or a combination of: performing optimizing data-fit correlation with variables comprising one or more of: valve size and type, parametric measurements from the first deformed analytical model data and the first anatomical model data, and performing variable normalization until an optimal correlation is reached; and predicting a likelihood of coronary obstruction event, with the optimal patient-specific predictive criteria.

2. The method of claim 1, further comprising: modeling blood flow, with the numerical analysis engine, around the aortic leaflet, through coronary ostium, and the virtually implanted trans-catheter valve of the first deformed analytical model, wherein the blood flow modeling is indicative of flow between the left and right coronary ostium, aortic leaflets, and the virtually implanted trans- catheter valve.

3. The method of claim 2, wherein the blood flow modeling comprises simulation of contrast dye flow pattern, and pressure gradient through the three dimensional gaps between the left and right coronary ostium, aortic leaflets, and the virtually implanted trans-catheter valve.

4. The method of claim 1, wherein the first anatomical model data comprises three-dimensional shapes of the anatomical regions of the heart including previously implanted surgical bioprosthetic heart valve, trans-catheter heart valves, or artificial root or stent grafts, and generating the first analytical model data based on the first anatomical model data, wherein the first analytical model data comprises a three-dimensional (3-D) mesh of the anatomical regions of the heart including a 3-D mesh of the previously implanted surgical bioprosthetic heart valve, trans-catheter valve, artificial root or stent graft.

5. The method of claim 1, further comprising: determining sensitivity of the trans-catheter valve relative to the patient's anatomy by:

generating a plurality of deformed analytical models based on the first analytical model data and based on a three-dimensional mesh of a virtually implanted trans-catheter valve, wherein each of the plurality of deformed analytical models is indicative of the sensitivity of anatomical regions of the heart and the respective plurality of deformed positions of the virtually implanted trans-catheter valve, wherein the generating of the plurality of deformed analytical model comprising:

varying the trans-catheter valve, deployment configurations comprising different depths, yaw, and pitch angles relative to a center line of an aortic root, and varying material properties of at least calcific nodules, leaflet tissue, and aorta tissue;

predicting a likelihood of coronary obstruction event for each configuration using the predictive criteria established from the existing database of image data from patients with and without coronary obstruction event after having implanted trans-catheter valves;

quantifying the sensitivity as the patient's risk of coronary obstruction with respect to variability in deployment configuration and material property.

6. The method of claim 1, wherein each of the respective gap sizes $\alpha_{2D1}$, $\alpha_{2D2}$ is determined based on: $\alpha_{2D} = \sqrt{(\Delta x)^2 + (\Delta y)^2}$ where $\Delta x = w - t$ and $\Delta y = h + d - 1$.

7. The method of claim 1, wherein predicting the likelihood of coronary obstruction event comprises determining a value of any of the respective gap sizes $\alpha_{2D1}$, $\alpha_{2D2}$ less than or equal to 4 millimeters (mm).

8. The method of claim 1, further comprising normalizing the respective gap sizes $\alpha_{2D1}$, $\alpha_{2D2}$ with a diameter of the coronary artery to determine a cut-off ratio.

9. The method of claim 8, wherein predicting the likelihood of coronary obstruction event comprises determining a value of the cut-off ratio less than or equal to 0.5.

10. The method of claim 1, wherein the image data comprises one of X-ray image data, magnetic resonance imaging (MRI) image data, and ultrasound image data.

11. A non-transitory computer readable medium having stored thereon, a computer program having at least one code section for predicting complications prior to an implantation of a trans-catheter valve in the heart, the at least one code section being executable by at least a processor, causing a machine to perform simulations comprising the steps of:

generating first anatomical model data based on image data characterizing anatomical regions of a heart of a patient, wherein the first anatomical model data comprises three-dimensional shapes of the anatomical regions of the heart comprising a left coronary leaflet, a right coronary leaflet, a non-coronary leaflet, an aortic root, left and right coronary ostia, an ascending aorta, and left and right coronary arteries;

generating first analytical model data based on the first anatomical model data, wherein the first analytical model data comprises a three-dimensional (3-D) mesh of the anatomical regions of the heart including at least parametric measurements comprising: a height h of coronary artery from an annulus baseline, a sinus width w at an ostium level, a thickness $t_1$ of a calcific nodule formed on the left coronary leaflet, a thicknesses $t_2$ of a calcific nodule formed on the right coronary leaflet, and a leaflet length of the left coronary leaflet and a leaflet length $l_2$ of the right coronary leaflet, and a coronary diameter d;

generating a first deformed analytical model based on the first analytical model data and based on a three-dimensional mesh of a virtually implanted trans-catheter valve, wherein the first deformed analytical model is indicative of a first deformed position of the anatomical regions of the heart and a first deformed position of the virtually implanted trans-catheter valve, wherein the generating of the first deformed analytical model comprising:

calculating respective gap sizes $\alpha_{2D1}$, $\alpha_{2D2}$ in a fully expanded configuration of the virtually implanted trans-catheter valve, wherein the $\alpha_{2D1}$, $\alpha_{2D2}$ are calculated using a parametric model based on the virtually implanted trans-catheter valve, each of the $\alpha_{2D1}$, $\alpha_{2D2}$ corresponds to a minimum two-dimensional distance between two points separated by a point Pc and an ostium point Po, wherein the point Pc corresponds to a nearest point on the left coronary leaflet and on the right coronary leaflet relative to Po, and the ostium point Po corresponds to an upper edge of the corresponding coronary ostium, and calculating respective gap sizes $\alpha_{3D1}$, $\alpha_{3D2}$ in the fully expanded configuration the virtually implanted trans-catheter valve, wherein the $\alpha_{3D1}$, $\alpha_{3D2}$ each corresponds to a respective minimum three-dimensional distance between the ostium point Po and the left coronary leaflet and on the right coronary leaflet, respectively;

establishing, from a database of image data from patients with and without coronary obstruction event after having implanted trans-catheter valves, a an optimal patient-specific predictive criteria of confirmed coronary obstruction, by performing systematic data-fitting on at least the respective gap sizes $\alpha_{2D1}, \alpha_{2D2}, \alpha_{3D1}, \alpha_{3D2}$ in combination with evaluating variables comprising one or more of: valve size and type, parametric measurements from the first deformed analytical model data and the first anatomical model data, wherein the first deformed analytical model data further correspond to the virtually implanted trans-catheter valve with full deployment configurations comprising different depths, yaw, and pitch angles relative to a center line of an aortic root, and wherein the performing of the systematic data-fitting with variables comprising one or more of: valve size and type, parametric measurements from the first deformed analytical model data and the first anatomical model data, and performing variable normalization until an optimal correlation is reached; and predicting a likelihood of coronary obstruction event, with the optimal patient-specific predictive criteria.

12. The non-transitory computer-readable medium according to claim 11, comprising code for modeling blood flow around the aortic leaflet, through coronary ostium, and the virtually implanted trans-catheter valve of the first deformed analytical model, wherein the blood flow modeling is indicative of flow into coronary ostium and then to coronary arteries through the three dimensional gaps between the left and right coronary ostium, aortic leaflets, and the virtually implanted trans-catheter valve.

13. The non-transitory computer-readable medium according to claim 12, wherein the blood flow modeling comprises simulation of contrast dye flow pattern, and pressure gradient through the three dimensional gaps between the left and right coronary ostium, aortic leaflets, and the virtually implanted trans-catheter valve.

14. The non-transitory computer-readable medium according to claim 11, wherein the first anatomical model data comprises three-dimensional shapes of the anatomical regions of the heart including previously implanted surgical bioprosthetic heart valve, trans- catheter heart valves, or artificial root or stent grafts, and generating the first analytical model data based on the first anatomical model data, wherein the first analytical model data comprises a three-dimensional (3-D) mesh of the anatomical regions of the heart including a 3-D mesh of the previously implanted surgical bioprosthetic heart valve, trans-catheter valve, artificial root or stent graft.

15. The non-transitory computer-readable medium according to claim 11, comprising code for determining sensitivity of the trans-catheter valve relative to the patient's anatomy by:

generating a plurality of deformed analytical models based on the first analytical model data and based on a three-dimensional mesh of a virtually implanted trans-catheter valve, wherein each of the plurality of deformed analytical models is indicative of the sensitivity of anatomical regions of the heart and the respective plurality of deformed positions of the virtually implanted trans-catheter valve, wherein the generating of the plurality of deformed analytical model comprising:

varying the trans-catheter valve deployment configurations comprising different depths, yaw, and pitch angles relative to a center line of an aortic root, and varying material properties of at least calcific nodules, leaflet tissue, and aorta tissue;

predicting a likelihood of coronary obstruction event for each configuration using the predictive criteria established from the existing database of image data from patients with and without coronary obstruction event after having implanted trans-catheter valves;

quantifying the sensitivity as the patient's risk of coronary obstruction with respect to variability in deployment configuration and material property.

16. The non-transitory computer-readable medium according to claim 11, wherein each of the respective gap sizes $\alpha_{2D1}, \alpha_{2D2}$ is determined based on: $\alpha_{2D} = \sqrt{(\Delta x)^2 + (\Delta y)^2}$, where $\Delta x = w - t$ and $\Delta y = h + d - l$.

17. The non-transitory computer-readable medium according to claim 11, predicting the likelihood of coronary obstruction event comprises determining a value of any of the respective gap sizes $\alpha_{2D1}, \alpha_{2D2}$ less than or equal to 4 millimeters (mm).

18. The non-transitory computer-readable medium according to claim 11, further comprising code for normalizing the respective gap sizes $\alpha_{2D1}, \alpha_{2D2}$ with a diameter of the coronary artery to determine a cut-off ratio.

19. The non-transitory computer-readable medium according to claim 18, wherein predicting the likelihood of coronary obstruction event comprises determining a value of the cut-off ratio less than or equal to 0.5.

20. The non-transitory computer-readable medium according to claim 11, wherein the image data comprises one of X-ray image data, magnetic resonance imaging (MRI) image data, and ultrasound image data.

* * * * *